United States Patent
Clark et al.

(10) Patent No.: US 11,623,215 B2
(45) Date of Patent: Apr. 11, 2023

(54) MULTIWELL PLATE WITH VARIABLE COMPRESSION SEAL

(71) Applicant: EMD Millipore Corporation, Burlington, MA (US)

(72) Inventors: Phillip Clark, Burlington, MA (US); Kurt E. Greenizen, Burlington, MA (US); John Doyle, Burlington, MA (US)

(73) Assignee: EMD Millipore Corporation, Burlington, MA (US)

( * ) Notice: Subject to any disclaimer, the term of this patent is extended or adjusted under 35 U.S.C. 154(b) by 663 days.

(21) Appl. No.: 16/607,743

(22) PCT Filed: May 10, 2018

(86) PCT No.: PCT/US2018/031958
§ 371 (c)(1),
(2) Date: Oct. 24, 2019

(87) PCT Pub. No.: WO2018/209020
PCT Pub. Date: Nov. 15, 2018

(65) Prior Publication Data
US 2020/0330981 A1   Oct. 22, 2020

Related U.S. Application Data

(60) Provisional application No. 62/668,908, filed on May 9, 2018, provisional application No. 62/551,268, filed
(Continued)

(51) Int. Cl.
*B01L 3/00* (2006.01)
*B01D 61/18* (2006.01)
(Continued)

(52) U.S. Cl.
CPC .......... *B01L 3/50255* (2013.01); *B01D 61/18* (2013.01); *B01D 61/58* (2013.01);
(Continued)

(58) Field of Classification Search
CPC ............. B01L 3/50255; B01L 2200/12; B01L 2300/041; B01L 2300/0681;
(Continued)

(56) References Cited

U.S. PATENT DOCUMENTS 3,175,850 A    3/1965   Steczynski
3,440,122 A    4/1969   McCormick
(Continued)

FOREIGN PATENT DOCUMENTS

CN    101652168 A    2/2010
CN    101820967 A    9/2010
(Continued)

OTHER PUBLICATIONS

European communication dated Dec. 9, 2020 in corresponding European patent application No. 18798068.5.
(Continued)

*Primary Examiner* — Joseph W Drodge
(74) *Attorney, Agent, or Firm* — Nields, Lemack & Frame, LLC

(57) ABSTRACT

Filtration apparatus for the assay of biological and biochemical reactants, for example, is provided and includes a substrate such as a plate having one or more wells open at each end, and a porous membrane positioned in each well forming a discrete filtering area. The filtration apparatus includes a seal that is in a compressible relationship with the face of the porous membrane, the surface of the compression element, and the well wall. Each well includes a compression element, such as an internal well insert or sleeve, which compresses the seal so that the seal contacts the membrane
(Continued)

face, the surface of the compression element, and the well wall in a liquid-tight manner. The compression element may be configured so that it is fixed in the well such as by an interference fit with the well wall or by bonding to a surface of the substrate.

32 Claims, 27 Drawing Sheets

Related U.S. Application Data on Aug. 29, 2017, provisional application No. 62/504,128, filed on May 10, 2017.

(51) Int. Cl.
  *B01D 61/58* (2006.01)
  *C07K 1/34* (2006.01)
(52) U.S. Cl.
  CPC .............. *C07K 1/34* (2013.01); *B01L 2200/12* (2013.01); *B01L 2300/041* (2013.01); *B01L 2300/0681* (2013.01); *B01L 2300/0829* (2013.01)
(58) Field of Classification Search
  CPC ....... B01L 2300/0829; B01L 2200/025; B01L 2200/0689; B01L 2300/0609; B01L 3/565; B01L 2200/0631; B01D 61/18; B01D 61/58; B01D 63/005; B01D 2313/025; B01D 2313/04; B01D 63/088; B01D 63/08; B01D 2313/02; C07K 1/34; G01N 1/40; G01N 1/4005; G01N 2035/00148; G01N 2035/00475
  See application file for complete search history.

(56) References Cited

U.S. PATENT DOCUMENTS

| | | | |
|---|---|---|---|
| 4,678,576 A | 7/1987 | Leoncavallo | |
| 4,702,834 A | 10/1987 | Relyea | |
| 4,832,840 A | 5/1989 | Klinkau et al. | |
| 5,141,719 A * | 8/1992 | Fernwood | B01D 61/18 422/549 |
| 5,564,177 A | 10/1996 | Fernandes et al. | |
| 5,603,900 A | 2/1997 | Clark et al. | |
| 5,741,463 A * | 4/1998 | Sanadi | B01L 3/5085 436/178 |
| 6,159,368 A * | 12/2000 | Moring | G01N 35/0099 422/258 |
| 6,309,605 B1 * | 10/2001 | Zermani | B01L 3/50255 422/535 |
| 6,896,849 B2 | 5/2005 | Reed et al. | |
| 8,021,455 B2 | 9/2011 | Adamek et al. | |
| 2001/0054584 A1 | 12/2001 | Bowers et al. | |
| 2002/0098125 A1 | 7/2002 | Roberts et al. | |
| 2002/0150505 A1 | 10/2002 | Reed et al. | |
| 2002/0195386 A1 * | 12/2002 | Young | B01L 3/50255 210/473 |
| 2003/0010708 A1 | 1/2003 | Leocavallo et al. | |
| 2003/0226796 A1 * | 12/2003 | Bayer, Jr. | B01L 3/50255 210/511 |
| 2004/0009583 A1 | 1/2004 | Benn et al. | |
| 2004/0149659 A1 * | 8/2004 | Kane | B01L 3/50255 210/453 |
| 2004/0188344 A1 | 9/2004 | Scott et al. | |
| 2004/0247490 A1 * | 12/2004 | Olivier | B01L 3/50255 422/513 |
| 2004/0265186 A1 | 12/2004 | Clark et al. | |
| 2004/0266023 A1 * | 12/2004 | Clark | B01L 3/50255 436/180 |
| 2005/0103703 A1 | 5/2005 | Young et al. | |
| 2006/0108287 A1 * | 5/2006 | Arnold | B01L 3/5085 210/651 |
| 2007/0098601 A1 * | 5/2007 | Mabuchi | B01L 3/5025 422/400 |
| 2007/0144959 A1 | 6/2007 | Zuk | |
| 2007/0151924 A1 | 7/2007 | Mir et al. | |
| 2009/0044702 A1 | 2/2009 | Adamek et al. | |
| 2009/0215150 A1 | 8/2009 | Kane et al. | |
| 2010/0151511 A1 * | 6/2010 | Greenizen | B01L 3/5085 435/395 |
| 2010/0233034 A1 * | 9/2010 | Olivier | B01L 3/50255 422/534 |
| 2010/0307967 A1 | 12/2010 | Clark et al. | |
| 2013/0264286 A1 | 10/2013 | Tai et al. | |
| 2013/0309147 A1 | 11/2013 | Yu | |
| 2013/0312501 A1 | 11/2013 | Dewey | |
| 2015/0108058 A1 | 4/2015 | Clark et al. | |
| 2015/0266630 A1 | 9/2015 | Scott et al. | |
| 2015/0283543 A1 | 10/2015 | McKean | |

FOREIGN PATENT DOCUMENTS

| | | | |
|---|---|---|---|
| DE | 8806971 U1 | 8/1988 | |
| EP | 1647329 A1 | 4/2006 | |
| JP | 2006-181567 A | 7/2006 | |
| JP | 2010-540239 A | 12/2010 | |
| WO | 2009/045268 A1 | 4/2009 | |
| WO | WO2010062310 A1 * | 6/2010 | ............. C12M 1/20 |
| WO | 2011/161480 A1 | 12/2011 | |
| WO | 2014/139139 A1 | 9/2014 | |

OTHER PUBLICATIONS

International Search Report and Written Opinion dated Sep. 24, 2018 in corresponding PCT application No. PCT/US2018/031958.
Japanese communication, with English translation, dated Jan. 5, 2021 in corresponding Japanese patent application No. 2019-561954.
Chinese communication, with English translation, dated Mar. 8, 2021 in corresponding Chinese patent application No. 201880046421.4.

\* cited by examiner

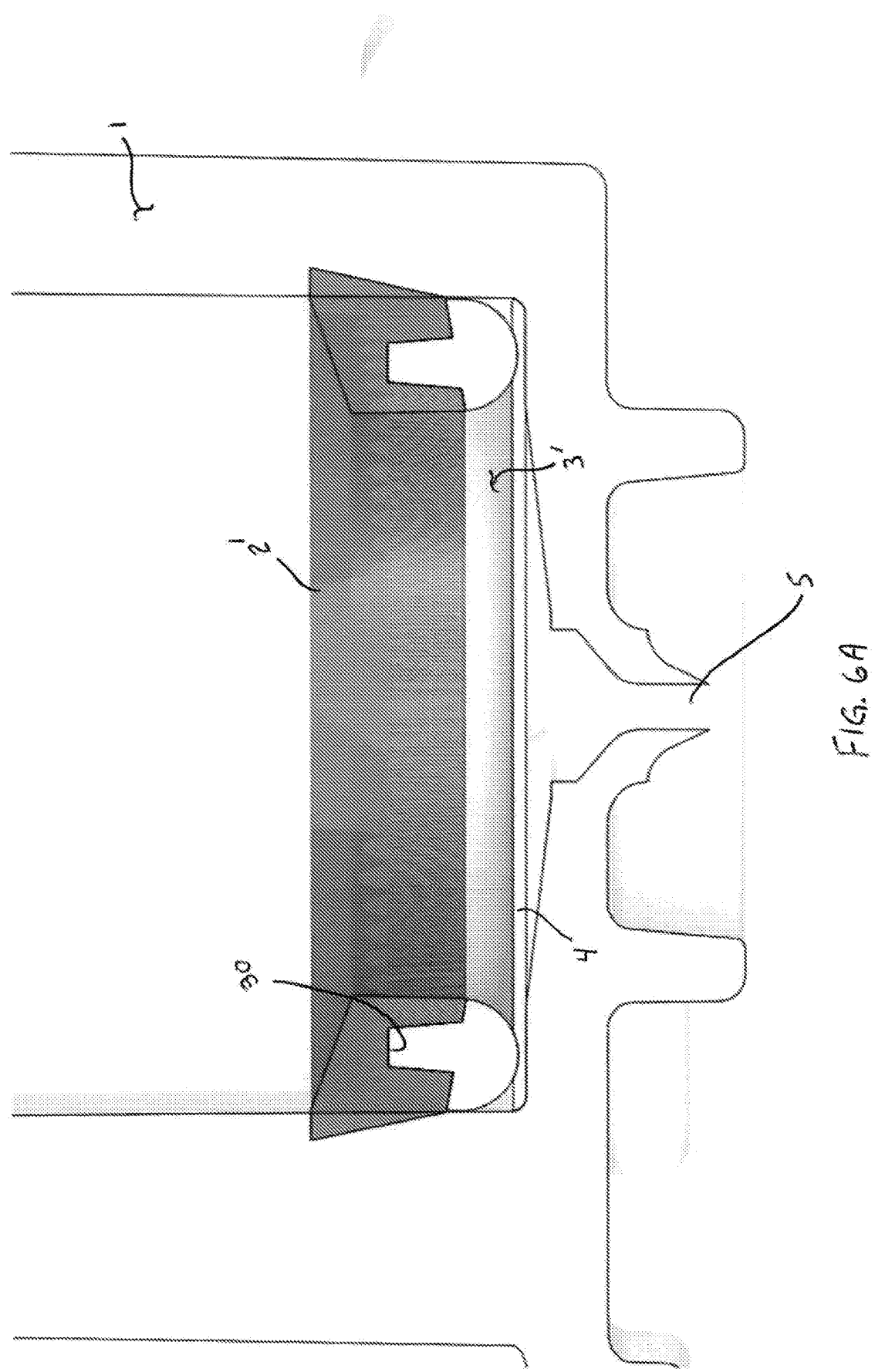

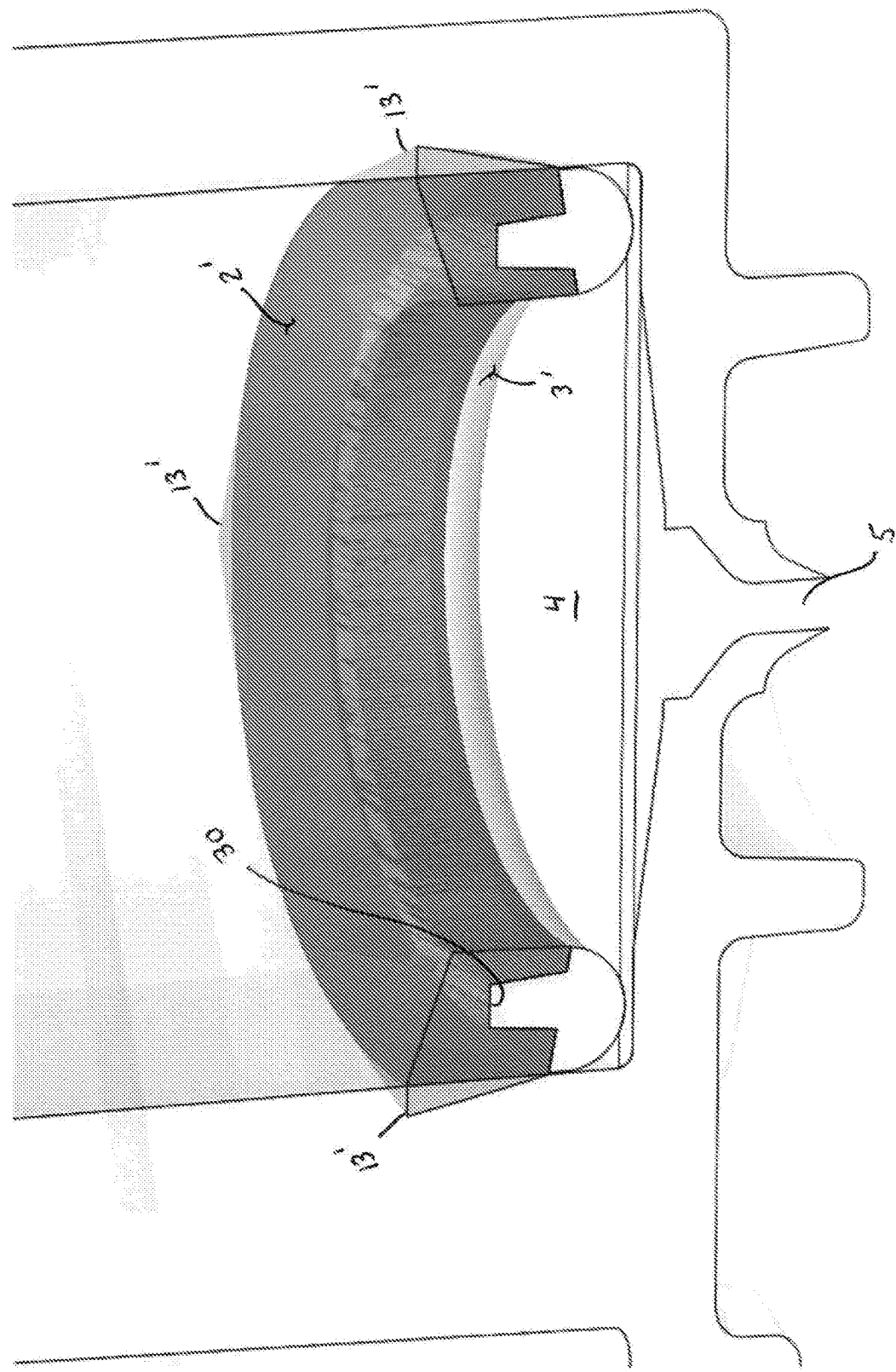

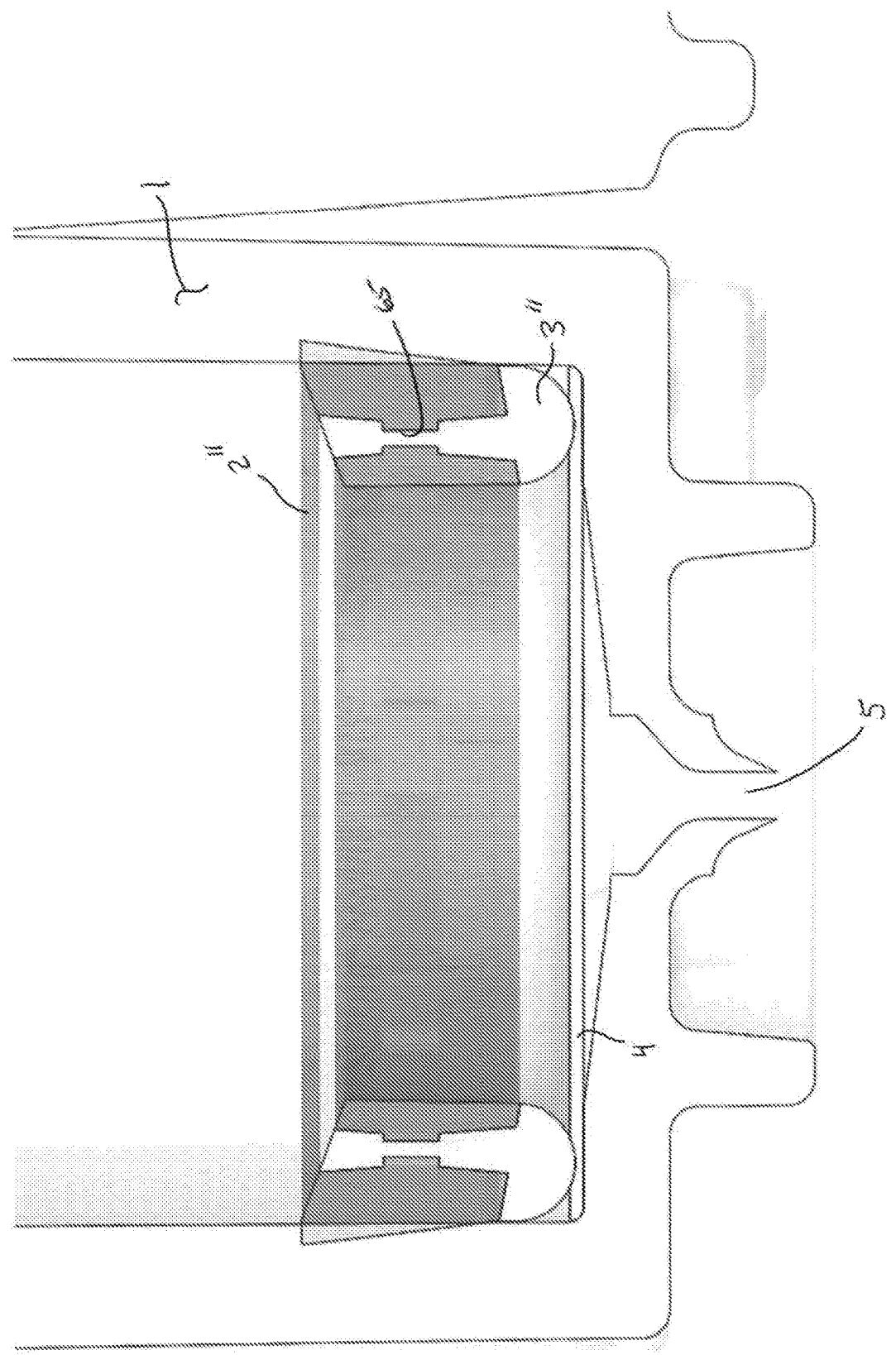

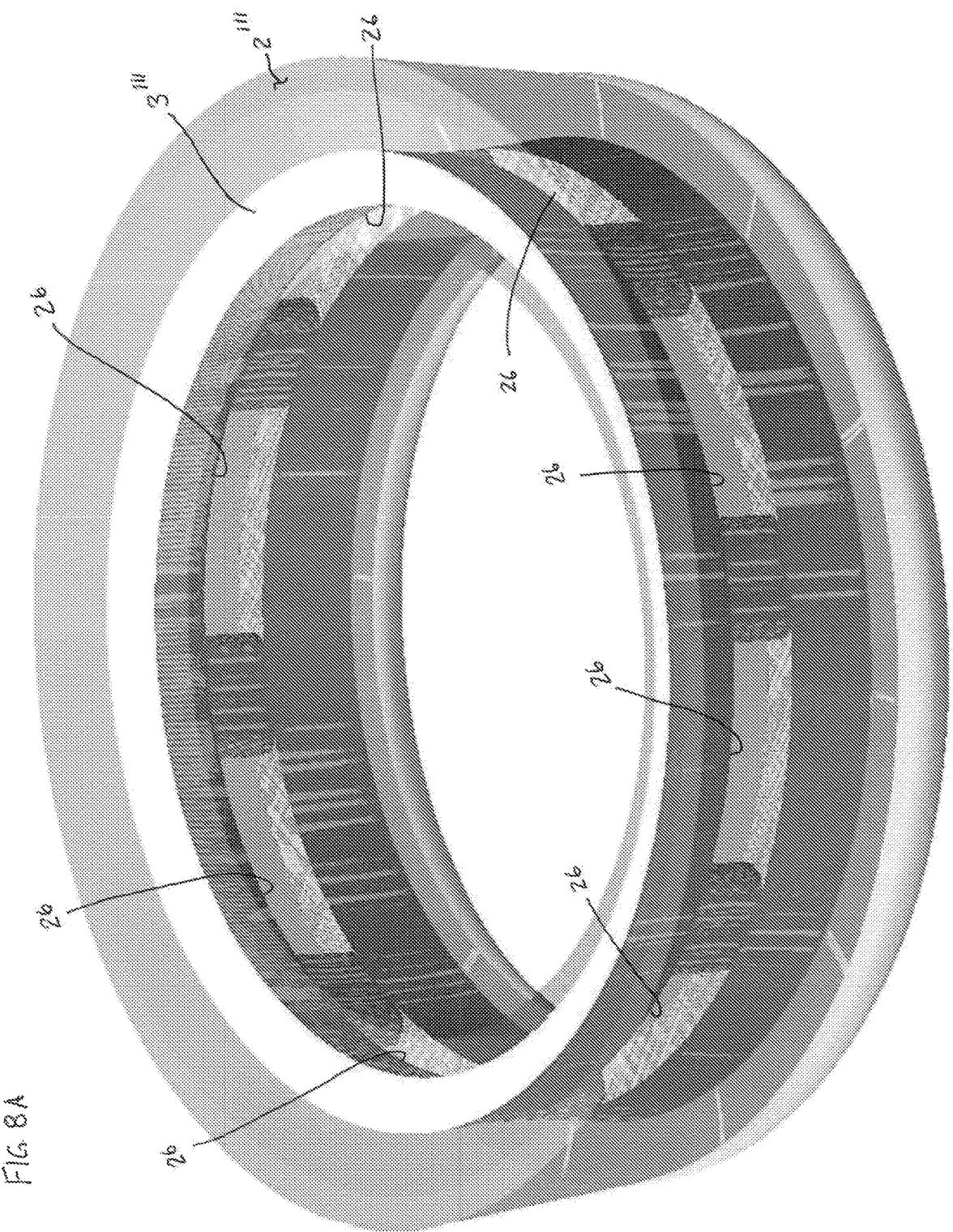

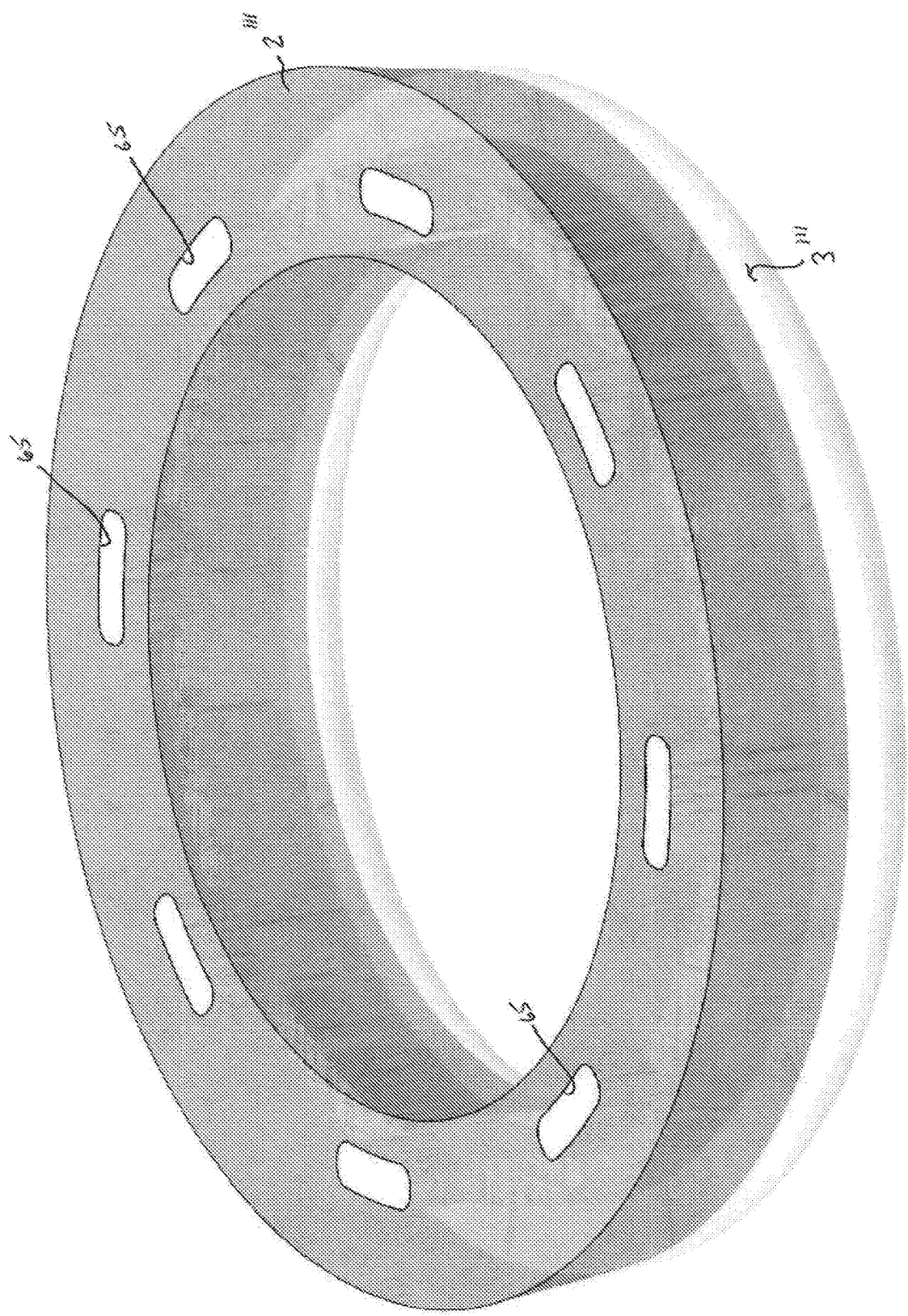

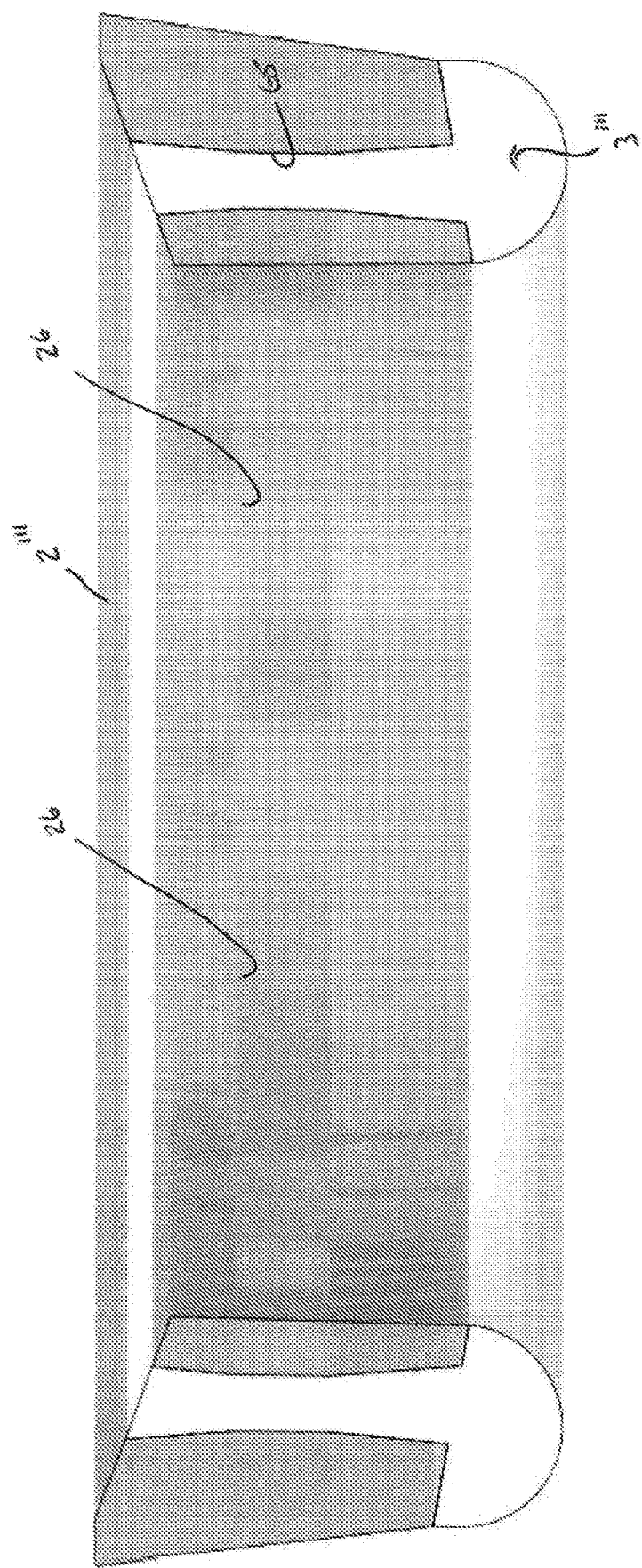

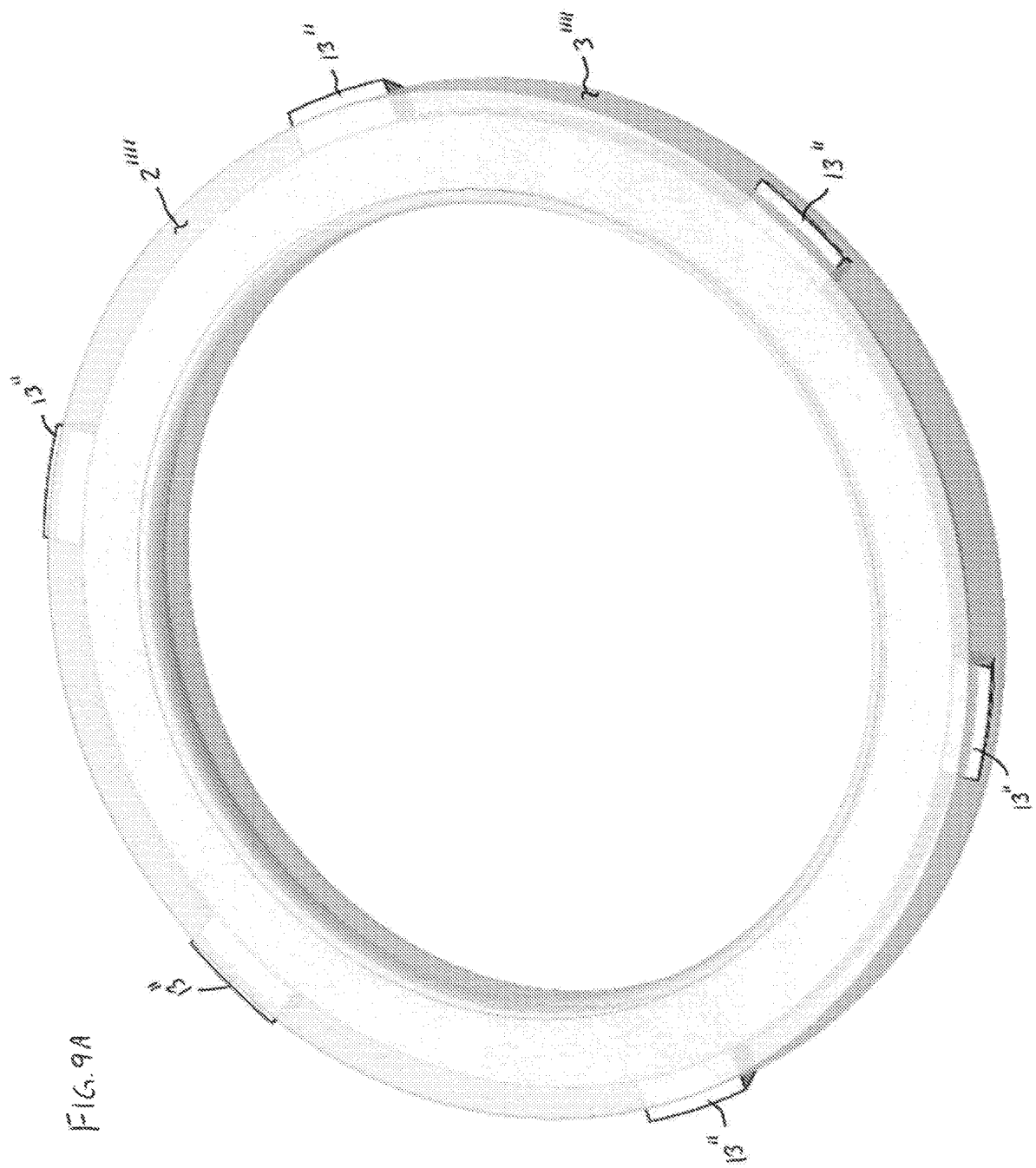

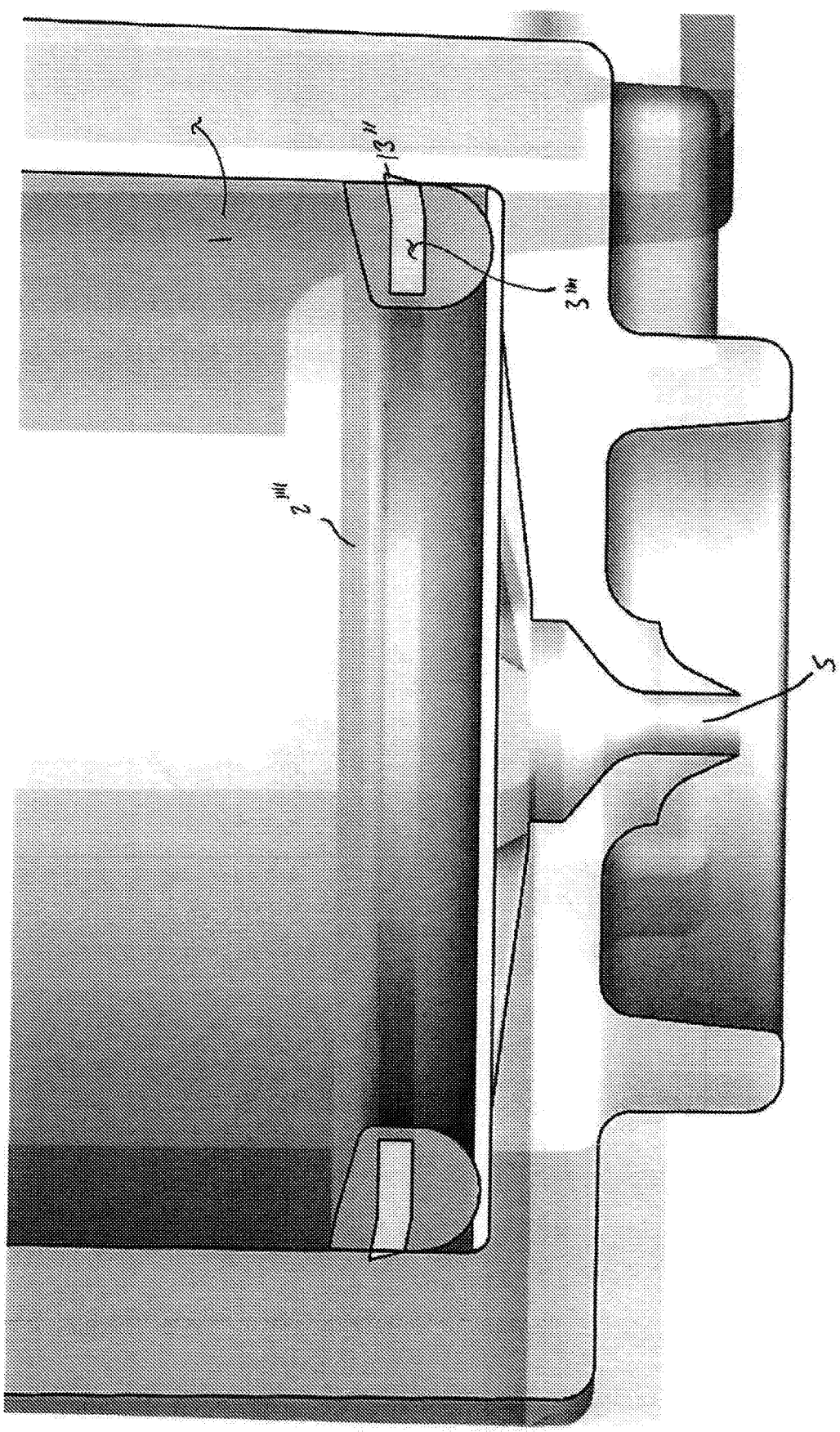

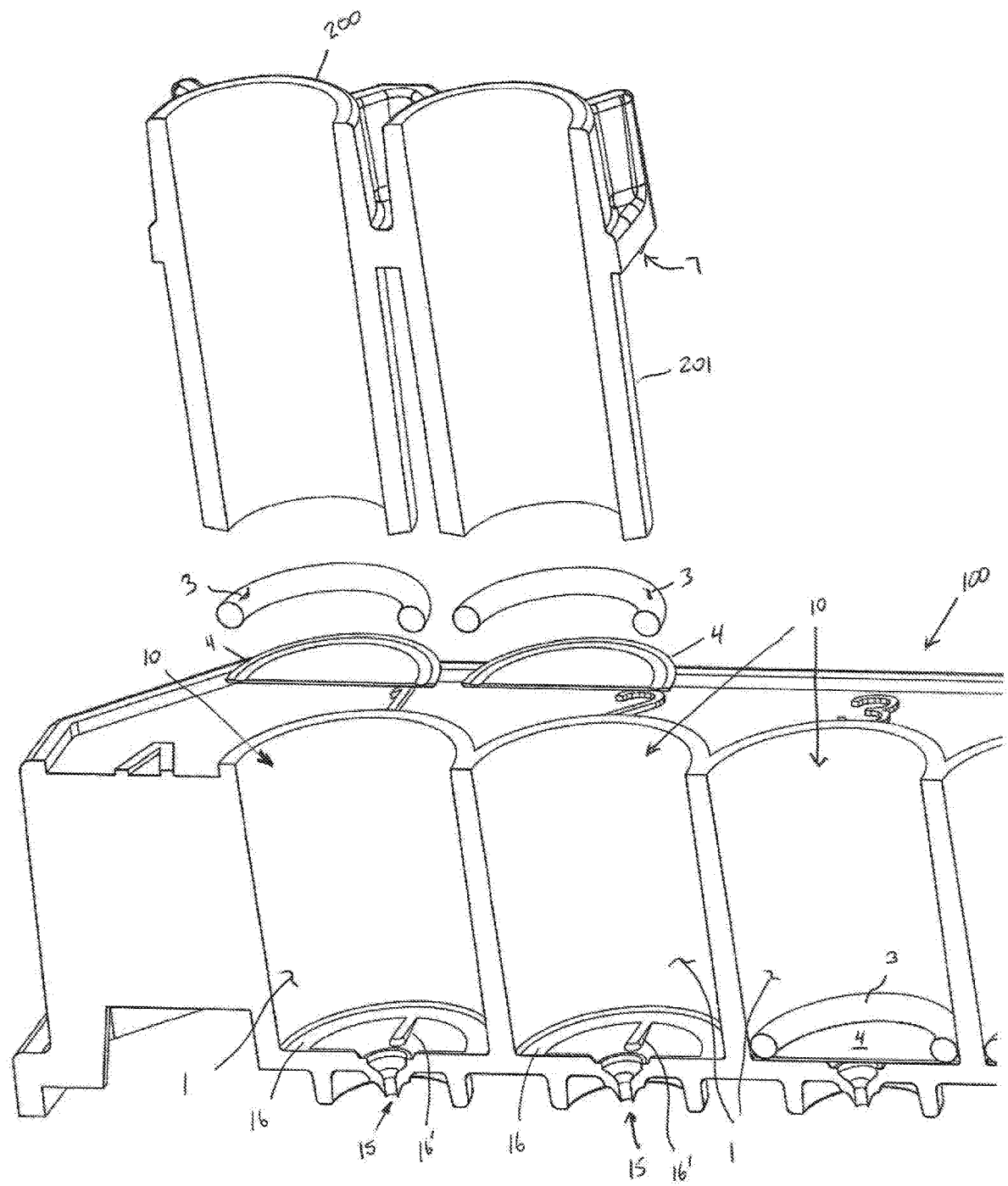

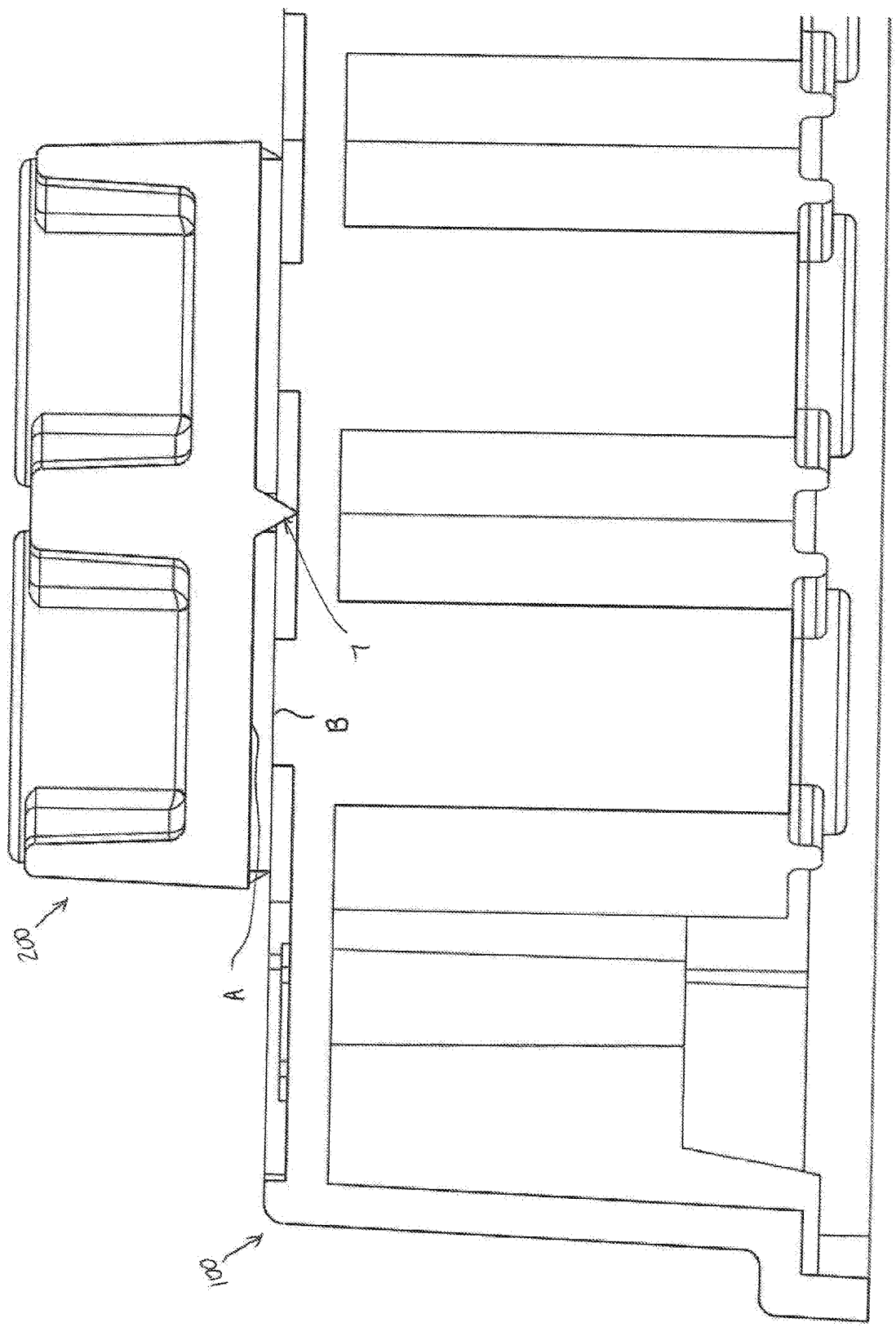

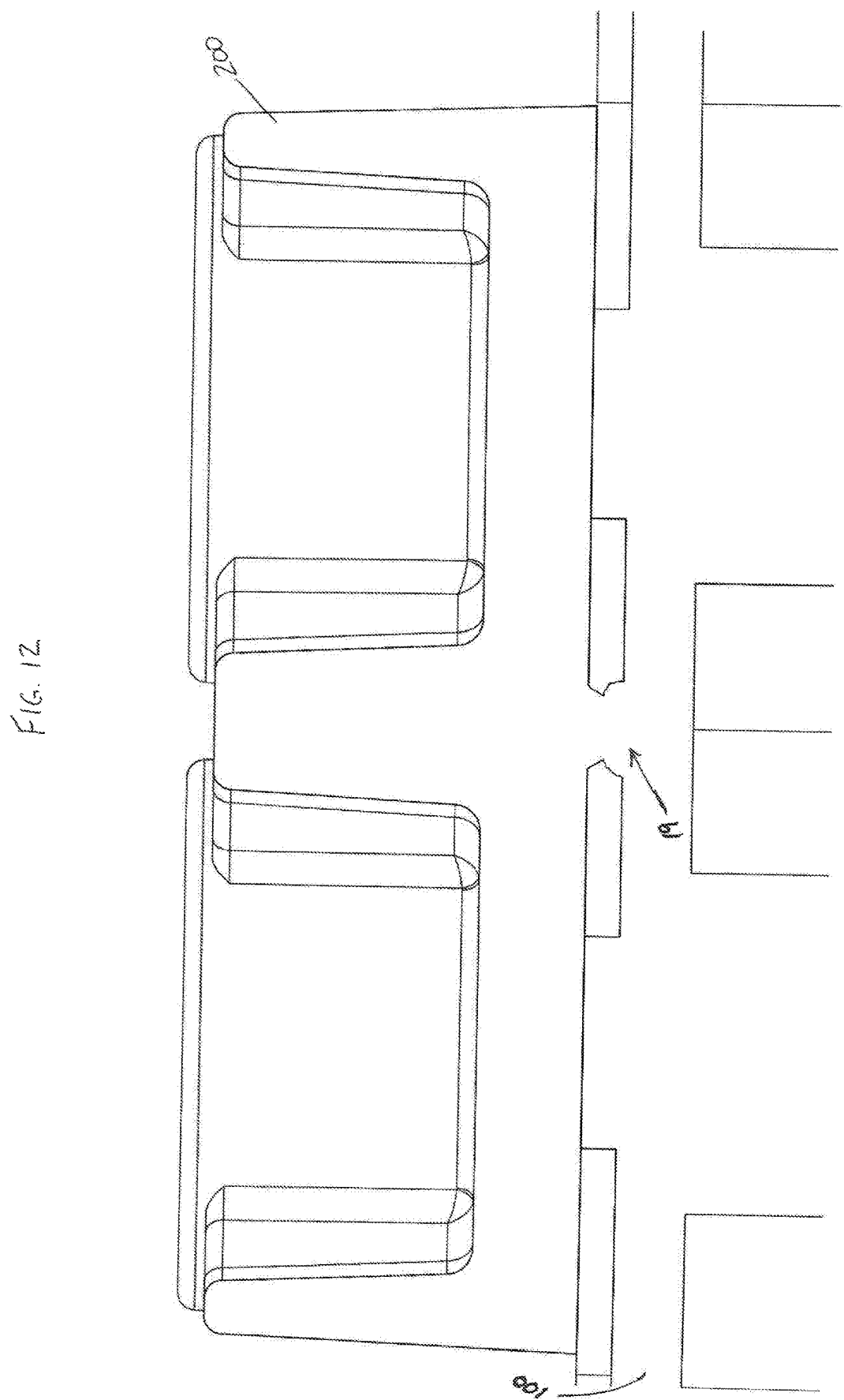

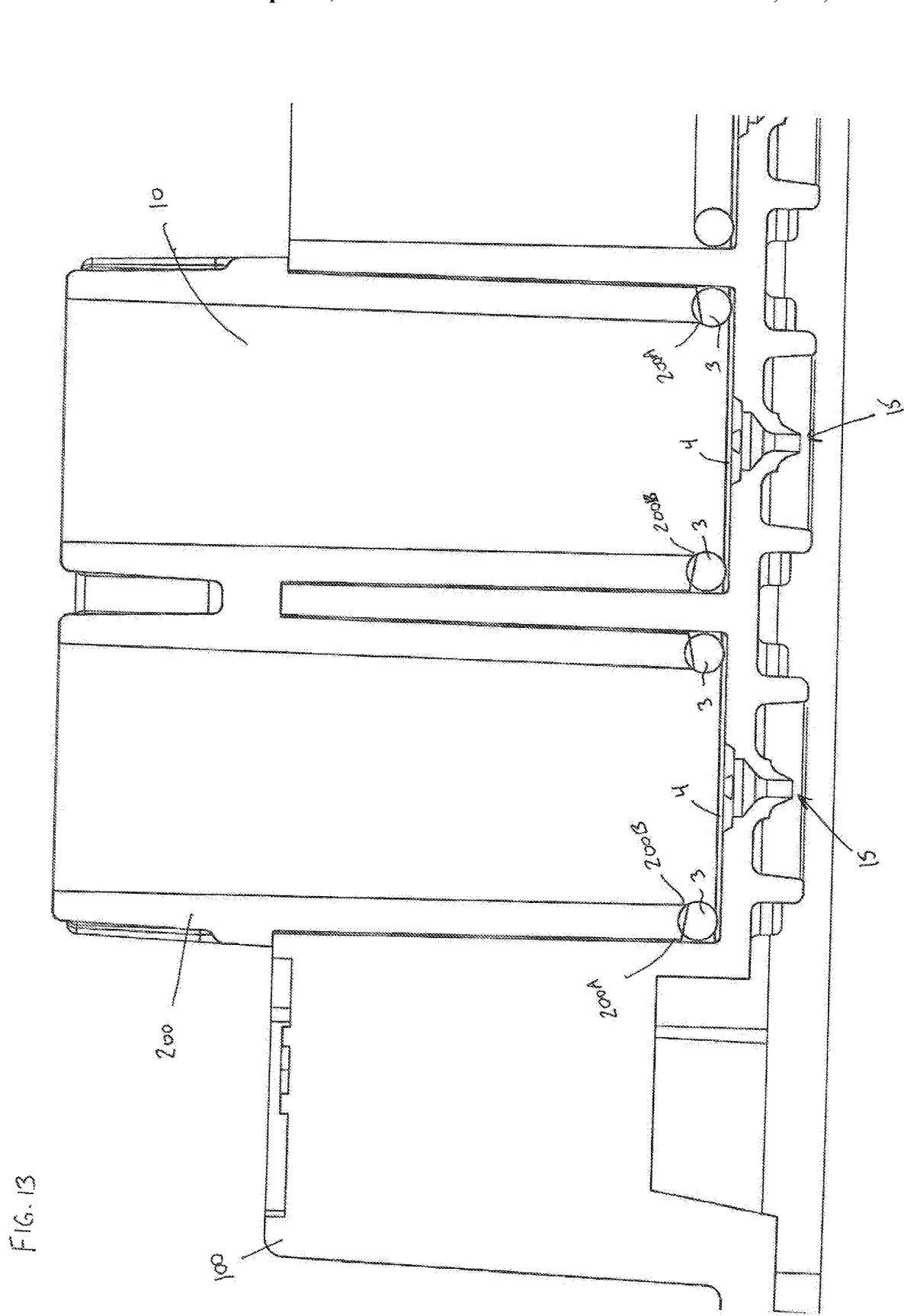

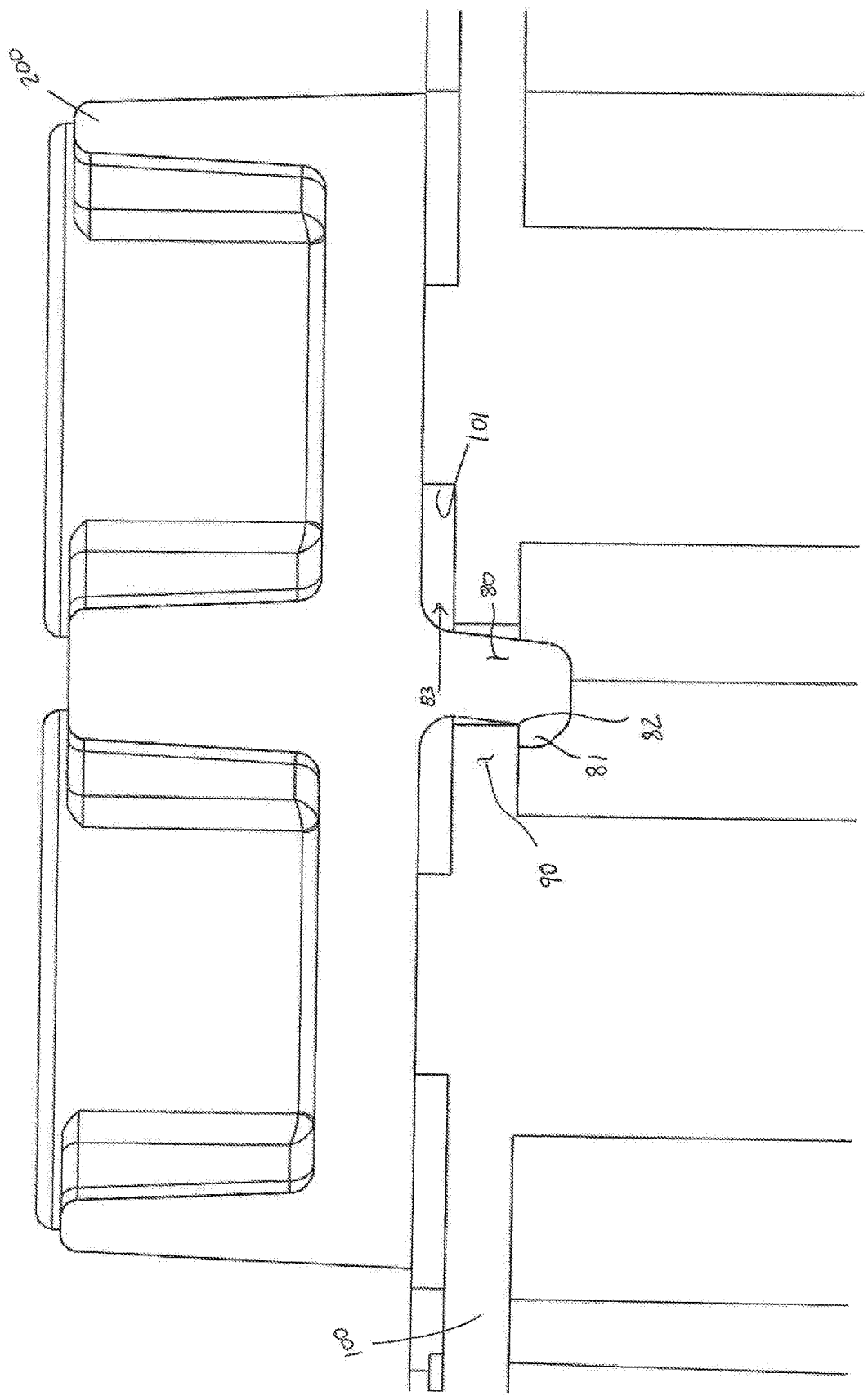

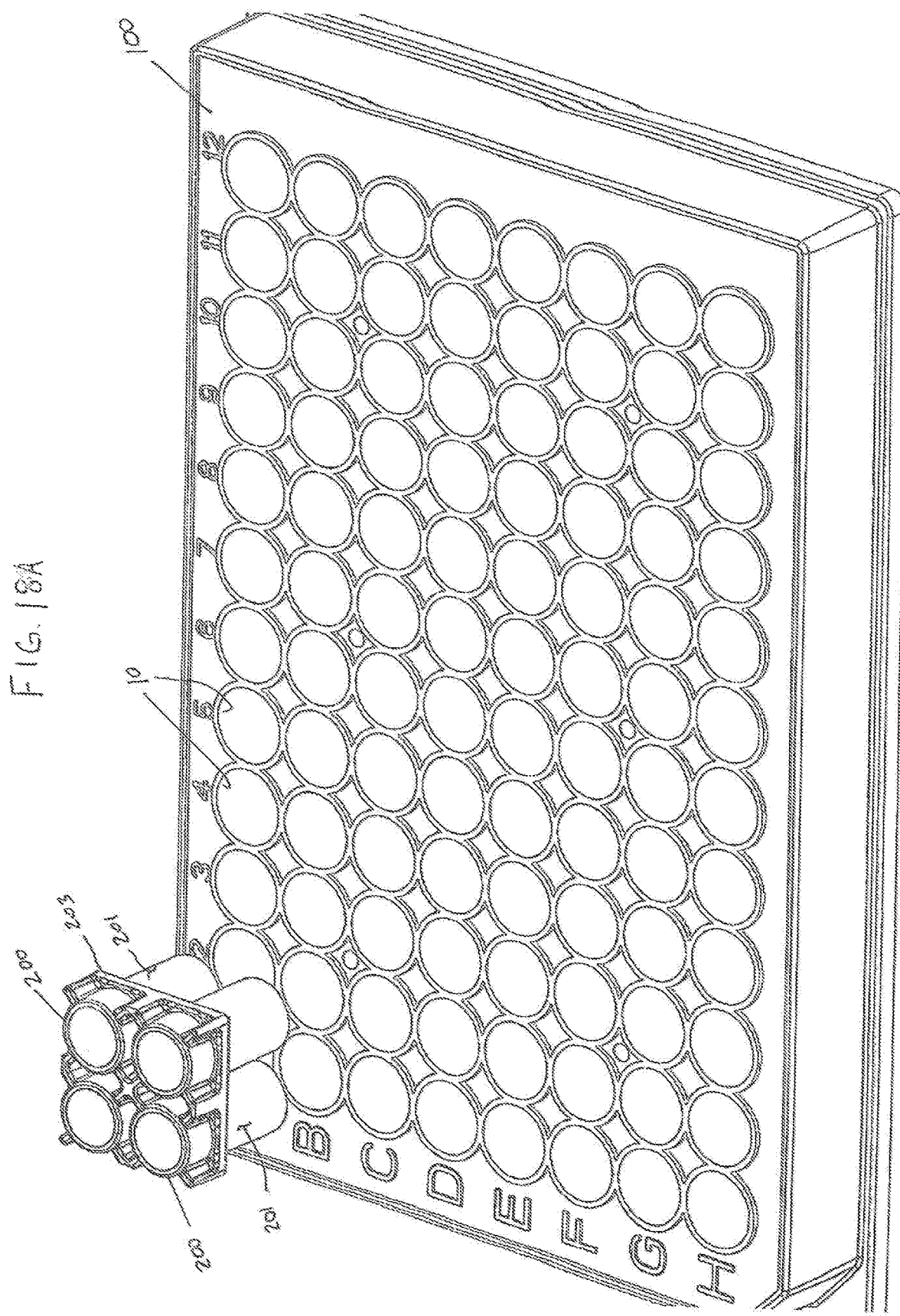

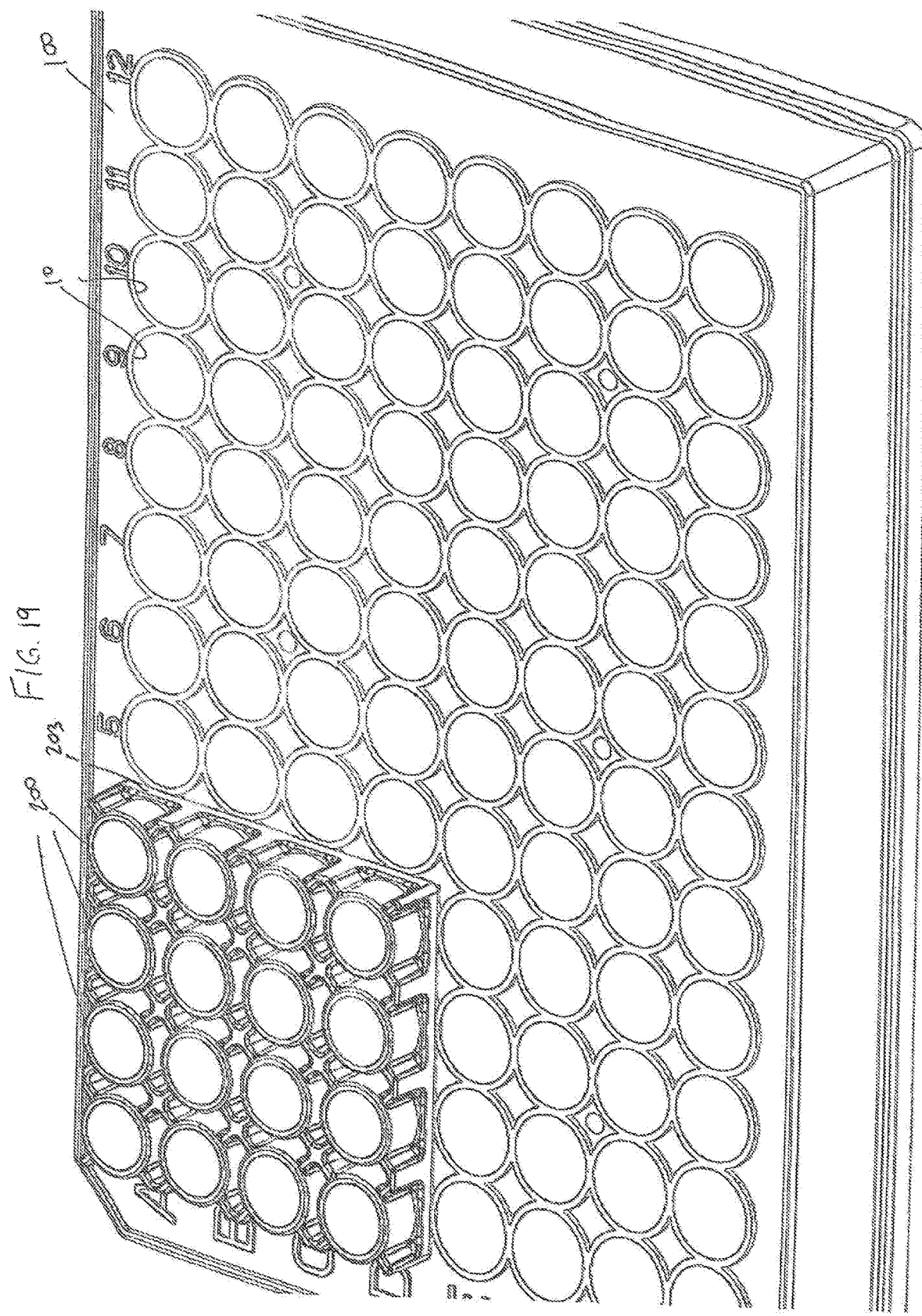

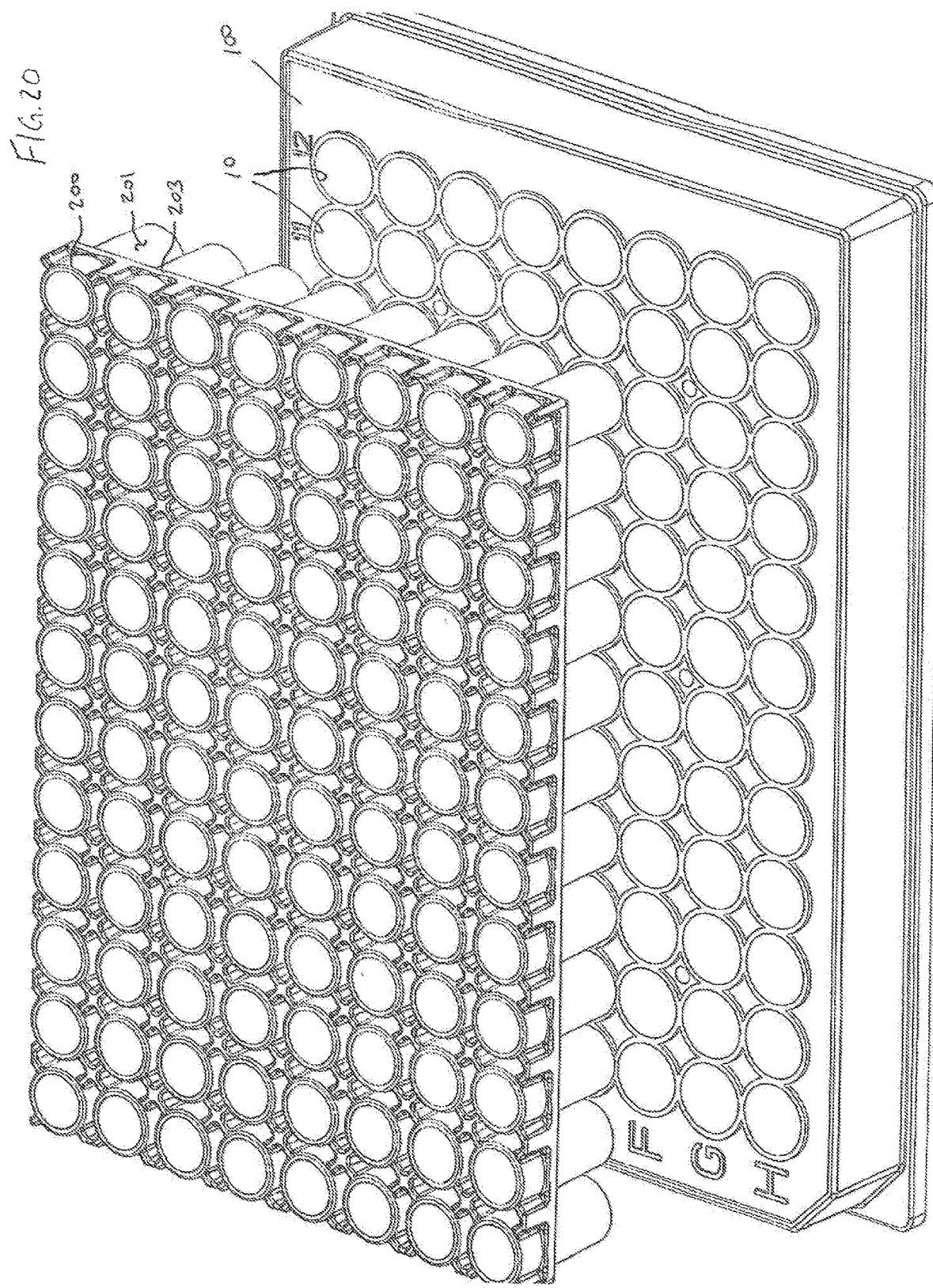

MULTIWELL PLATE WITH VARIABLE COMPRESSION SEAL

This application claims priority of provisional application Ser. Nos. 62/504,128 filed on May 10, 2017, 62/551,268 filed on Aug. 29, 2017, and 62/668,908 filed on May 9, 2018, the disclosures of each of which are hereby incorporated by reference.

BACKGROUND

Embodiments disclosed herein generally relate to laboratory apparatus useful in the assay of, for example, biological and biochemical reactants and is particularly concerned with multiwell filtration devices. More specifically, embodiments disclosed herein relates to multiwell filtration device wherein the sample filtration process is driven by a pressure differential across the membrane, the pressure differential is created by applying a negative or positive pressure to one side of the filter or by a centrifugal force.

The use of multiwell plates to, for example, filter and purify various products such as proteins, DNA, RNA, plasmids, small molecules and the like or for use in drug screening or drug discovery in the laboratory is widespread. Advantages include the ability to use small volumes of samples required, especially with experimental compounds or with the screening of 1000s of potential compounds, and the ability to run multiple samples at the same time. A growing segment of drug discovery is more and more sample testing in a cost-effective way, which means automated liquid handling robots and multiwell plates that process multiple samples at a time. Most plate-based systems are arranged to have a filter plate positioned above a collection plate. Typical filters plates have a series of wells, e.g., 96 or 384 or 1536, arranged in orderly rows and columns. The bottom of each well has an opening that is selectively covered by one or more porous filters or membranes. The membranes are typically hydrophilic to allow for the passage of fluids through them at a relatively low amount of force. In some instances the membrane can be hydrophobic, but a higher pressure is required to initiate flow. The collection plate typically has the same number of wells as the filter plate and they are aligned with the filter plate wells so that they collect the fluid from the respective well above it. The bottom of the collection plate wells is generally closed.

The fluid in the filter plate must pass through the filter or membrane before reaching the collection plate well. Most filter plates also contain an underdrain below the filter or membrane. The underdrain may contain a spout or the like to direct the fluid from the filter plate to the well of the collection plate below it. It may also contains some type of sloped surface to cause the fluid in the underdrain to move toward the spout. A driving force, such as vacuum, may be fluidly connected to the system to draw the fluid through the filter plate and underdrain and into the collection plate. Additionally, pressure can be used as the driving force.

Typically, a 96-well filtration plate format is used to conduct multiple assays simultaneously, some of which last several hours before filtration is completed. A challenge to all manufacturers of filter plates fabricated with an ultrafiltration membrane, is the material of the membrane makes conventional sealing methods result in less than desirable manufacturing processes and high performance variability in the resulting product. The most common sealing methods are classic heat sealing, ultrasonic welding and the use of a sealing gasket.

Heat sealing has been tried and ultimately has resulted in some commercial ultrafiltration membrane plates. The assembly consists of positioning 96 discs of membranes into the bottom of each well of the 96 well polypropylene plate. A heat platen with 96 extended heated cylinders is moved to thermally fuse the underside of the membrane to the bottom inner surface of each well. Time, temperature and force are the controlling process variables. However, each membrane type requires a unique set of processing parameters. Most efforts result in an unacceptable bond.

Ultrasonic welding has been used in a few plates that have been commercialized, but not with an ultrafiltration membrane. An open bottom multiwell plate and mating underdrain structure designed to collect and direct the resulting filtrate to a receiving well are aligned. A single sheet of filter material membrane is positioned between the plate and the underdrain covering all of the well openings. An ultrasonic welder compresses the three piece assembly and actuates the ultrasonic action. The ultrasonic system does two things in this process. First, the plate and underdrain shear the membrane sheet into 96 discs. Second, the ultrasonic energy melts the plate and underdrain to fuse them together and in doing so, the membrane discs are captured between the well and underdrain outlet, resulting in 96 discrete wells.

A gasketing element has proven the most successful when sealing the difficult UF membranes. The basic construction is a base element that has a support grid, a disc of membrane positioned on the support grid, a gasket (flat gasket or O-ring) positions on the membrane and finally the sample receiver is snapped together with the base. When the elements are snapped or fused together, the gasket is compressed a defined amount to seal against the membrane face. When the sample liquid is dispensed into the well and a driving force is applied, the sample passes through the membrane and out the grid in the base to be collected.

One benefit to a gasket seal is that it is independent of the membrane materials of construction and membrane chemistry. The only limiting factor is the gauge thickness of the membrane, although the resilient nature of the elastomeric seal offers some flexibility for variations in membrane thickness. Currently a reliable multiwell plate with an ultrafiltration membrane has not been successfully commercialized. There are several single sample devices a with an ultrafiltration membranes, a few examples are MICROCON® and CENTRICON® devices from MiiliporeSigma in Bedford Mass.

A growing segment of the drug discovery research market, in both the academic and pharmaceutical environments, has a demand for higher throughput, cost effective sample testing. Typically, this translates to the use of automated liquid handling robots and multiwell plates that process 96 or more samples at a time. A UF plate is an excellent platform to investigate free versus bound drugs, which is an important characteristic for a drug development. For example, to test a drug compound of interest, the drug is spiked into a blood product such as serum and then filtered by a UF membrane. The serum and other proteins are retained by the membrane so the small molecule drug passes through the filter and is collected and tested. Drugs found in the filtrate are considered free and may be available to work on the target of interest.

A significant problem that needs to be addressed, however, is reliable sealing of an ultrafiltration membrane in a way that protein presented into each well of a multiwell format is reliably retained and the small molecules pass through the membrane to be collected.

It therefore would be desirable to provide an alternative sealing method for sealing ultrafiltration membranes in a multiwell plate format.

It also would be desirable to provide a method of sealing the membrane that is independent of membrane pore size, membrane material and/or membrane chemistry.

It also would be desirable to provide a method of sealing a membrane that can be adjusted for different membrane thicknesses.

It also would be desirable to provide a method of sealing a membrane that is suitable for multiwell plates, such as plates with 12, 24, 96 and 384 wells.

SUMMARY

A filtration apparatus for the assay of biological and biochemical reactants, for example, is provided and comprises a substrate such as a substrate or plate having a one or more wells open at each end, and a porous membrane positioned in each well forming a discrete filtering area. In certain embodiments, the filtration apparatus includes a seal or sealing member that is in a compressible relationship with the face of the porous membrane and the well wall. In certain embodiments, the seal is a sealing gasket positioned on the membrane in the well. In certain embodiments, each well includes a compression element that compresses the seal or sealing member so that it contacts both the membrane face and the well wall. In certain embodiments, each well includes a compression element that compresses the seal or sealing member so that it contacts both the membrane face and the lower face of the compression element itself, thereby preventing liquid from accessing the region along the well wall during operation. In certain embodiments, the compression element is an internal well insert configured to be disposed in a well and positioned within the well to compress the seal. In certain embodiments, the internal well insert is bonded to a support surface of the well of the well plate in which the well is formed, permanently affixing the internal well insert in place in the device.

In some embodiments, the compression element is configured so that it is fixed in the well such as by an interference fit with the well wall, or is bonded to a support surface of the well of the well plate in which the well is formed, permanently affixing it in place.

In some embodiments the filtration apparatus comprises a substrate having at least one well defined by a well wall and having a first opening and a second opening spaced from the first opening and defining a volume there between; a porous filter material in the at least one well, positioned in the at least one well so as to cover the second opening; a seal or sealing member in the at least one well positioned on a portion of the porous filter; and a compression element fixed in the at least one well in a position to compress the sealing member into sealing relationship with the porous filter and the wall of the at least one well.

Also disclosed is a method of assembling the filtration apparatus discussed above, and a method of sealing one or more membranes in a filtration apparatus, such as a single well or multiwell filtration device. For example, in certain embodiments, a method of sealing one or more membranes in a filtration apparatus, such as a single well or multiwall filtration device, may include die cutting a membrane disc and placing it at the bottom of a well of a filtration device, covering the filtrate outlet. A seal or sealing member may be positioned on top of the membrane, and a compression element may be inserted into the well. In some embodiments, the insertion of the compression element is complete when the seal is compressed against the membrane and the well wall. In some embodiments, a surface of an internal well inert or sleeve is bonded or otherwise affixed to a support surface of the substrate to hold the inert or sleeve in position. It is then able to apply a force to the sealing member, pushing the sealing member outwardly to seal to the well wall inside surface.

In some embodiment, an interference fit of the compression element and the well wall allows it to hold its position. In other embodiments, a surface of the compression element is bonded or otherwise affixed to a support surface of the substrate to hold the compression element in position. It is then able to apply a force to the sealing member, pushing the sealing member outwardly to seal to the well wall inside diameter.

Also disclosed is a method of filtering a sample with a filtration device that includes a substrate having at least one well defined by a well wall and having a first opening and a second opening spaced from the first opening and defining a volume there between, a porous filter material in the at least one well, positioned in the at least one well so as to cover the second opening, a seal in the at least one well positioned on a portion of the porous filter, and an internal well insert coupled to the substrate and disposed within the at least one well; the internal well insert having a wall that abuts against the well wall, wherein the method comprises introducing the sample into the internal well insert, and filtering the sample through the porous filter material. A driving force, such as vacuum or pressure, may be used to facilitate filtration.

In some embodiments, a filtration element is disclosed, the filtration element comprising a substrate having a plurality of wells, each well defined by a fluid impervious well wall and having a first opening and a second opening spaced from the first opening and defining a well volume there between; a porous filter material disposed in each well, positioned in each well so as to cover the second opening; a seal in each well positioned on a portion of the porous filter; a plurality of internal well inserts coupled to the substrate, the number of internal well inserts corresponding to the number of the wells of the plurality of wells, each internal well insert having a region disposed in a respective well and positioned in its respective well so as to compress the seal into sealing relationship with the porous filter and the well wall. In certain embodiments, at least some of the plurality of internal well inserts are coupled to one another in an array.

BRIEF DESCRIPTION OF THE DRAWINGS

FIG. 6A is a sectional view of an integrated compression element and sealing member positioned in a well in accordance with certain embodiments;

FIG. 6B is a sectional view of an alternative integrated compression element and sealing member positioned in a well in accordance with certain embodiments;

FIG. 7 is a sectional view of yet another integrated compression element and sealing member positioned in a well in accordance with certain embodiments;

FIG. 8A is a top perspective view of yet another integrated compression element and sealing member positioned in a well in accordance with certain embodiments;

FIG. 8B is a bottom perspective view of the integrated compression element and sealing member of FIG. 8A;

FIG. 8C is a sectional view of the integrated compression element and sealing member of FIG. 8A;

FIG. 9A is a top perspective view of yet another integrated compression element and sealing member positioned in a well in accordance with certain embodiments;

FIG. 9C is a sectional view of the integrated compression element and sealing member of FIG. 9A positioned in a well;

FIG. 10 is an exploded perspective partial view of a multiwell device having a sealing gasket and a compression element that is an internal well sleeve or insert in accordance with certain embodiments;

FIG. 11 is a cross-sectional view of an internal well sleeve or insert positioned in a multiwall device in accordance with certain embodiments;

FIG. 12 is a cross-sectional view of an internal well insert thermally fused to a substrate in accordance with certain embodiments;

FIG. 13 is a cross-sectional view showing an internal well sleeve or insert compressing a seal in accordance with certain embodiments;

FIG. 14 is a cross-sectional view of an internal well sleeve or insert with a snap feature for attaching it to a well substrate in accordance with certain embodiments;

FIG. 18A is a perspective view of a multiwell plate with a 2×2 array of internal well sleeves or inserts shown just prior to introduction into respective wells in accordance with certain embodiments;

FIG. 19 is a perspective view of a multiwell plate with a 4×4 array of internal well sleeves or inserts shown inserted into respective wells in accordance with certain embodiments;

FIG. 20 is a perspective view of a multiwell plate with a 12×8 array of internal well sleeves or inserts shown just prior to introduction into respective wells in accordance with certain embodiments.

DETAILED DESCRIPTION

Figure 1:
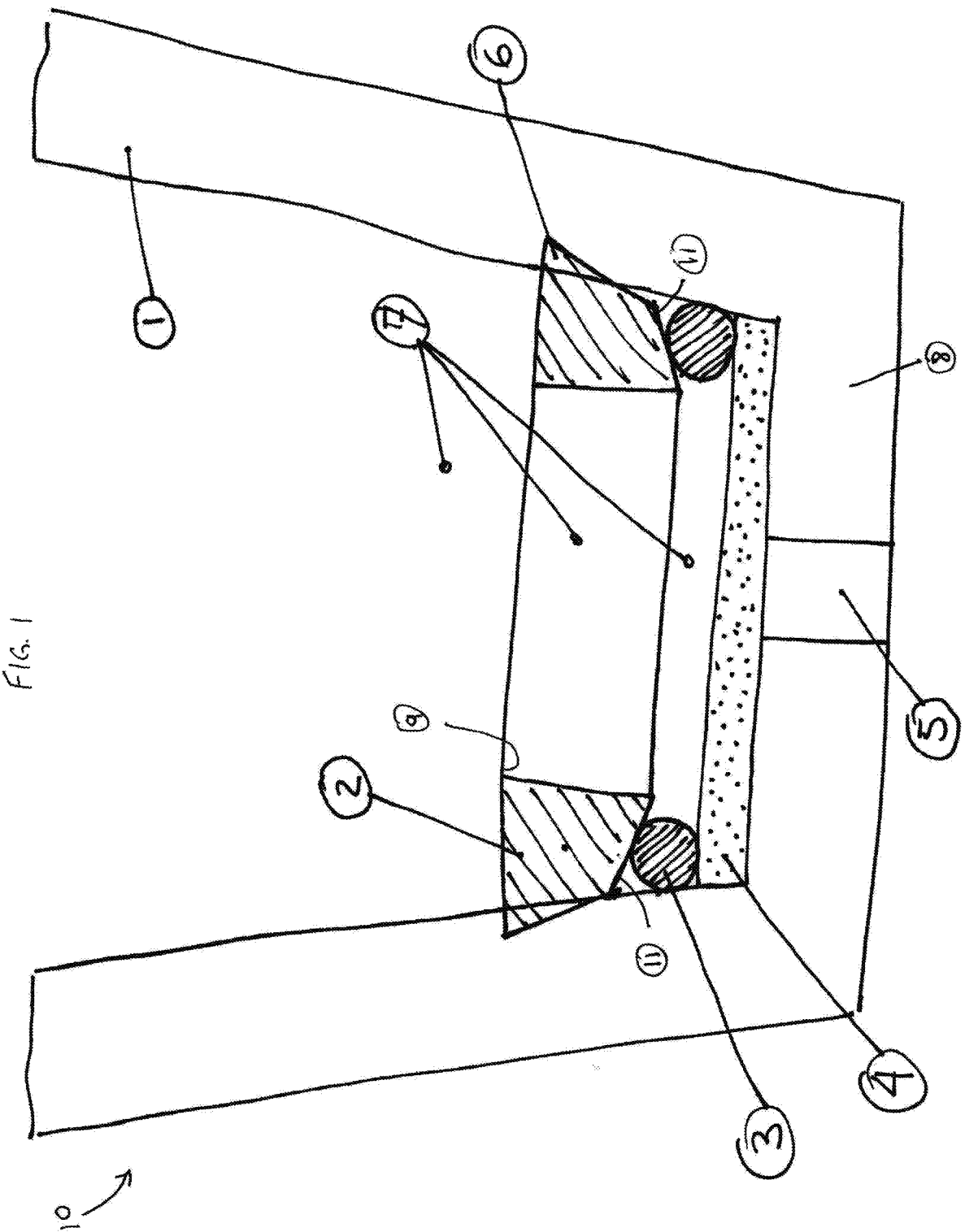
FIG. 1 is a cross-sectional view of a well having a sealing gasket and compression element in accordance with certain embodiments.

A more complete understanding of the components, processes and apparatuses disclosed herein can be obtained by reference to the accompanying drawings. The figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the general structure of the embodiments selected for illustration in the drawing, and are not intended to define or limit the scope of the disclosure. In the drawing and the following description below, it is to be understood that like numeric designations refer to components of like function.

The singular forms "a," "an," and "the" include plural referents unless the context clearly dictates otherwise.

As used in the specification, various devices and parts may be described as "comprising" other components. The terms "comprise(s)," "include(s)," "having," "has," "can," "contain(s)," and variants thereof, as used herein, are intended to be open-ended transitional phrases, terms, or words that do not preclude the possibility of additional components.

It should be noted that many of the terms used herein are relative terms. For example, the terms "upper" and "lower" are relative to each other in location, i.e. an upper component is located at a higher elevation than a lower component, and should not be construed as requiring a particular orientation or location of the structure.

The terms "top" and "bottom" are relative to an absolute reference, i.e. the surface of the earth. Put another way, a top location is always located at a higher elevation than a bottom location, toward the surface of the earth.

Figure 2:
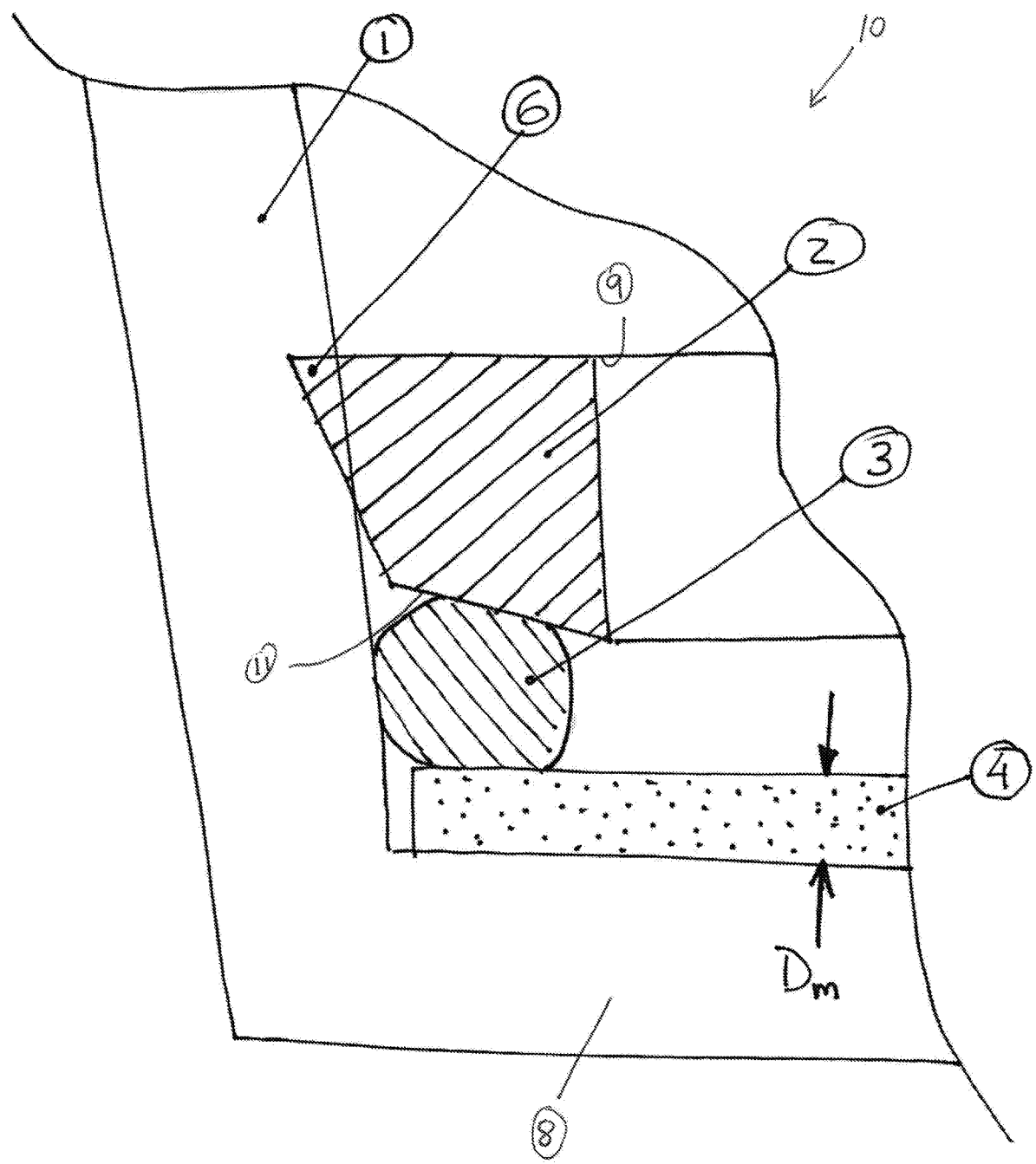
FIG. 2 is an enlarged view of a portion of the well of FIG. 1 in accordance with certain embodiments.

Turning now to FIGS. 1 and 2, there is shown an embodiment of a well 10 which may be part of a multiwell filtration device 100, or may be a well in a single well filtration device. The well 10 is defined by a fluid impervious wall 1, which is preferably funnel-shaped such that it tapers inwardly, preferably in a uniform manner, from the open inlet towards the bottom surface 8 having outlet 5. In one embodiment, the well has a taper of 0.5 degrees per side, which results in a diameter difference in the region of the interference (the bottom quarter of the well) of 0.004 inches. An interference of as little 0.005 inches and as much as 0.025 inches can be used. The device may be made of a material not deleterious to the sample being filtered, such as polypropylene which exhibits low protein binding.

In certain embodiments, a sealing member 3, such as a pliable gasket or O-ring, is positioned in compressive relationship with the top surface or face of a porous membrane 4 supported on the bottom surface 8. In certain embodiments a compression element 2 is positioned in the well 10 to compress the sealing member 3 so that the sealing member 3 contacts both the porous membrane 4 and the well wall 1. In some embodiments the compression element 2 is configured so that it has an interference fit within the well 10, contacting the well wall 1 to effectively hold it in place to retain the compression forces on the sealing member 3. The positional relationship between the compression element 2 and the sealing member 3 is maintained; the force to compress the sealing member 3 is insufficient to move the compression member 2 out of position. The compression element 2 thus functions to hold it in place in the well, apply a force to the sealing member 3 so that it seals on the face of the porous membrane 4, and push the sealing member radially outwardly to seal against the well wall 1 inside diameter so that liquid sample cannot flow around the porous membrane 4 and out the outlet 5 without passing through the porous membrane 4. The compression element 2 has one or more apertures 9 (one central aperture shown)

for flow of fluid. Element 7 indicates regions within the well 10 that liquid sample can occupy.

In certain embodiments, the compression element 2 has a larger diameter than the inside diameter of the well 1 in the location in the well 1 where the compression element 2 is held. Preferably the compression element 2 is constructed of a material that is harder than the material from which the well is made. This difference in hardness enables the compression element 2 to interfere with the well wall 1. Suitable materials for the compression element 2 include plastic, metal, glass and epoxy, provided that the material used is harder than the well wall 1. One suitable material for the compression element is polycarbonate, where the well wall is polypropylene.

In some embodiments, the compression element 2 is configured to be trapezoidal in cross-section, such that its outer diameter at or near its top surface is larger than the outside diameter at the bottom surface. This provides a slight lead angle that facilitates sliding the compression element 2 into the well using a push force, and provides a sharp back edge 6 that interferes with the well wall 1 to inhibit removal of the compression element 2 from the well, thereby ensuring that its position in the well 1 is maintained.

In certain embodiments, the face of the compression element 2 that is in contact with the sealing element 3 may be sloped at 11. This slope is to bias the sealing element 3 to seal to the well wall and to the membrane 4 when compressed. A suitable slope is greater than 5 degrees and preferably 30 degrees.

The thickness $D_m$ of the membrane 4 can vary, because of the ability to change the insertion depth while still achieving a reliable seal to the membrane 4 and the well wall 1. The $D_m$ thickness can be an assembly of more than one membrane layer. The individual layers of membrane can be the same or can be differing by pore size, chemistry or construction.

In certain embodiments, the interference feature of the compression element 2 is an uninterrupted interference edge; that is, the outer diameter of the region of the compression element 2 that interferes with the well wall 1 is constant throughout the entire perimeter of that region. In other embodiments, the interference feature of the compression element 2 is an interrupted interference edge; that is, the outer diameter of the region of the compression element 2 that interferes with the well wall 1 is not throughout the entire perimeter of that region.

One method to assembly a filtration device is as follows. A membrane 4 is die cut into a disc and placed at the bottom of a well 10, covering the well outlet 5. A sealing element 3 such as a gasket or an O-ring is positioned on top of the membrane 4 in the well 10. A compression element 2 is inserted into the well 10 to a location in the well 10 where it compresses against the sealing element 3, causing the sealing element 3 to compress against the membrane 4 and the well wall 1.

Figure 3:
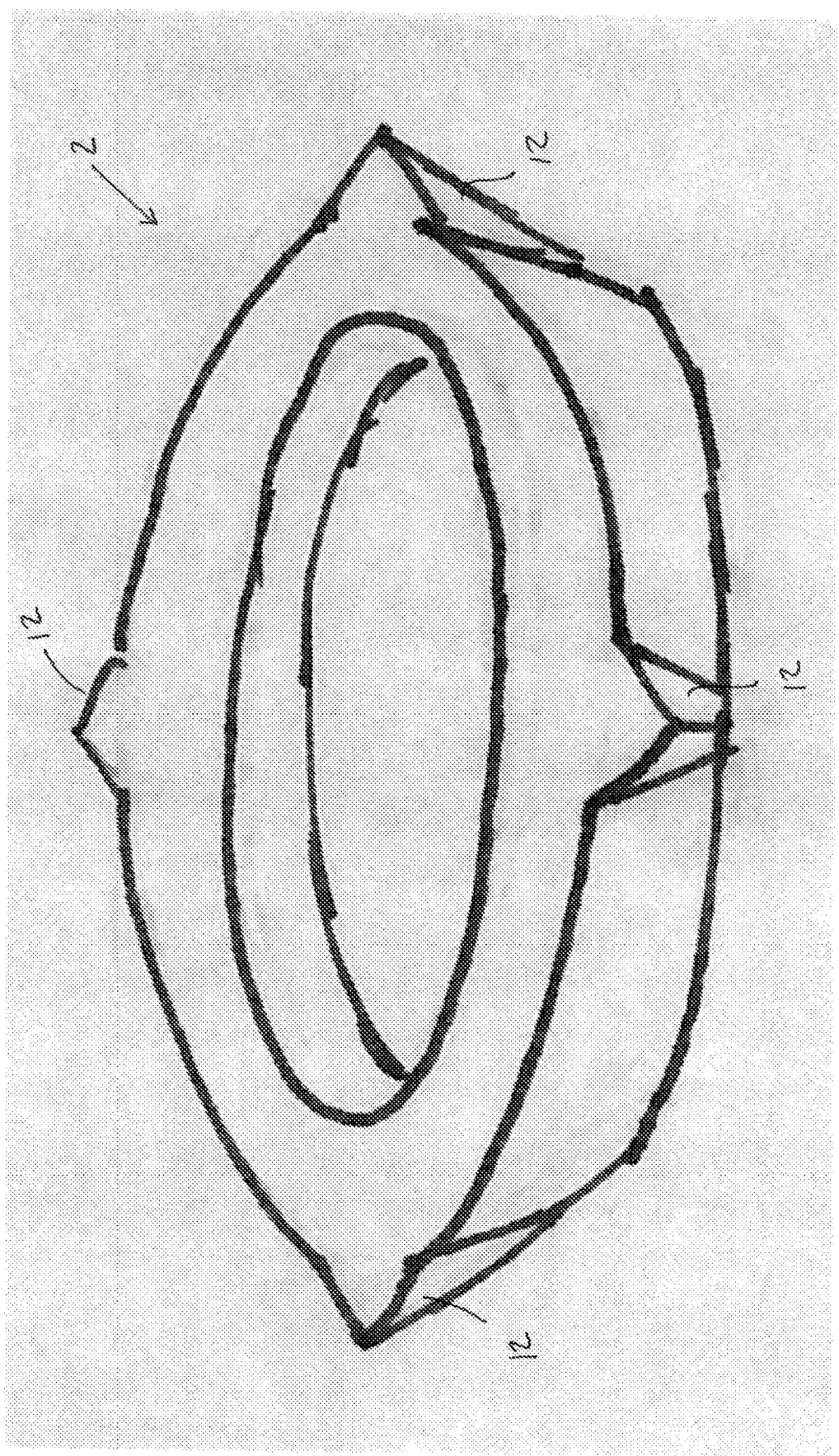
FIG. 3 is a perspective view of a compression element in accordance with certain embodiments.

FIG. 3 illustrates one embodiment of an interrupted interference edge, where the compression element 2 includes a plurality of radial protrusions 12 that extend radially outwardly from the main body of the compression element as shown. In the embodiment shown, there are four spaced radial protrusions 12, although those skilled in the art will appreciate that fewer or more could be present. Preferably the radial protrusions 12 are equally spaced from one another. In some embodiments, the radial protrusions 12 are triangular in section so that they are generally wedged shaped, and taper radially inwardly from the top surface of the compression element 2 toward the bottom surface.

Figure 4:
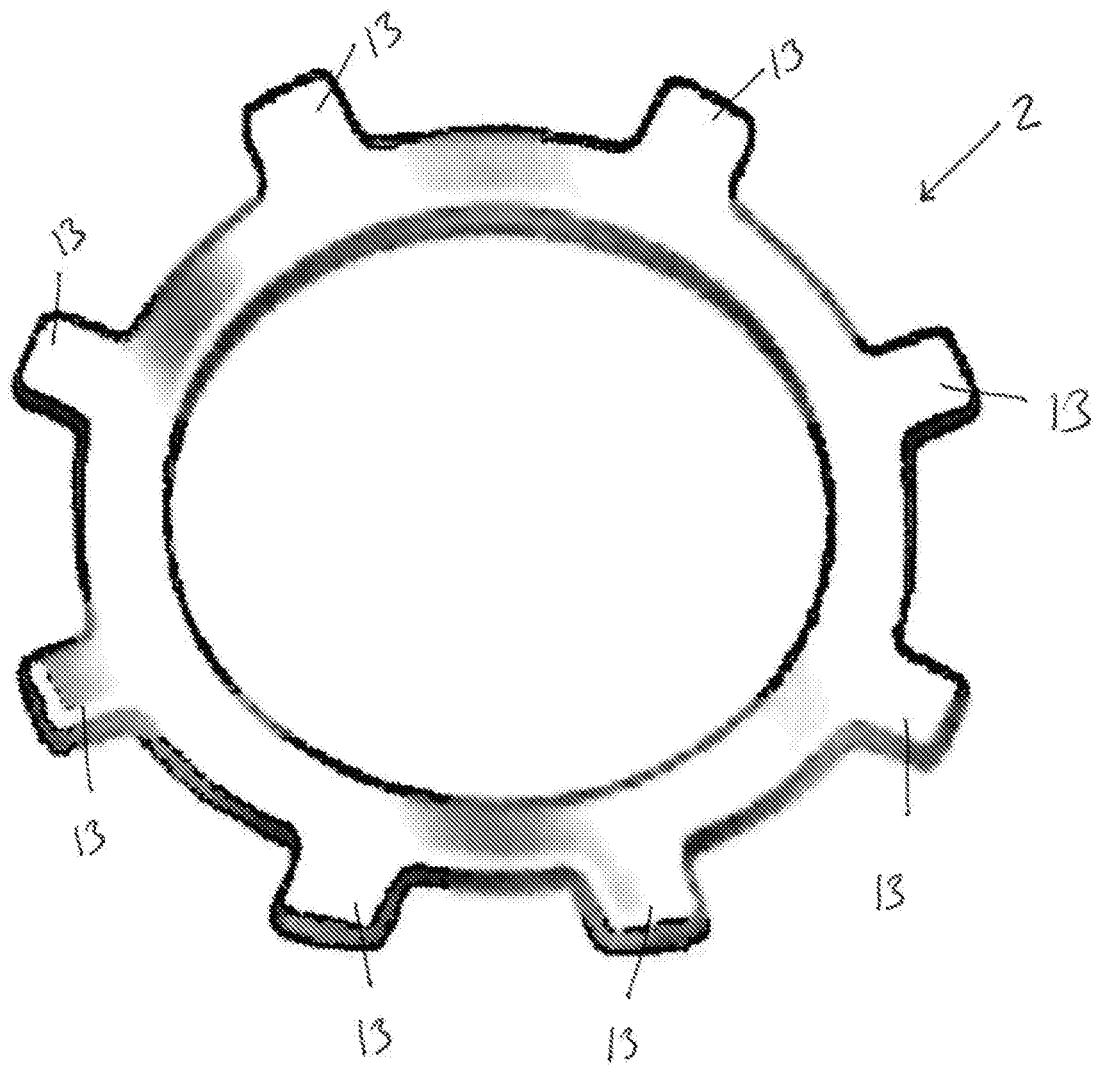
FIG. 4 is a perspective view of another compression element in accordance with certain embodiments.

FIG. 4 illustrates another embodiment of a compression element 2 with an interrupted interference edge, wherein the compression element 2 includes a plurality of radial protrusions 13 that extend radially outwardly from the main body of the compression element as shown. The radial protrusions 13 are generally flat and act as radial teeth. In the embodiment shown, there are eight spaced radial protrusions 13, although those skilled in the art will appreciate that fewer or more could be present. Preferably the radial protrusions 13 are equally spaced from one another.

Figure 5:
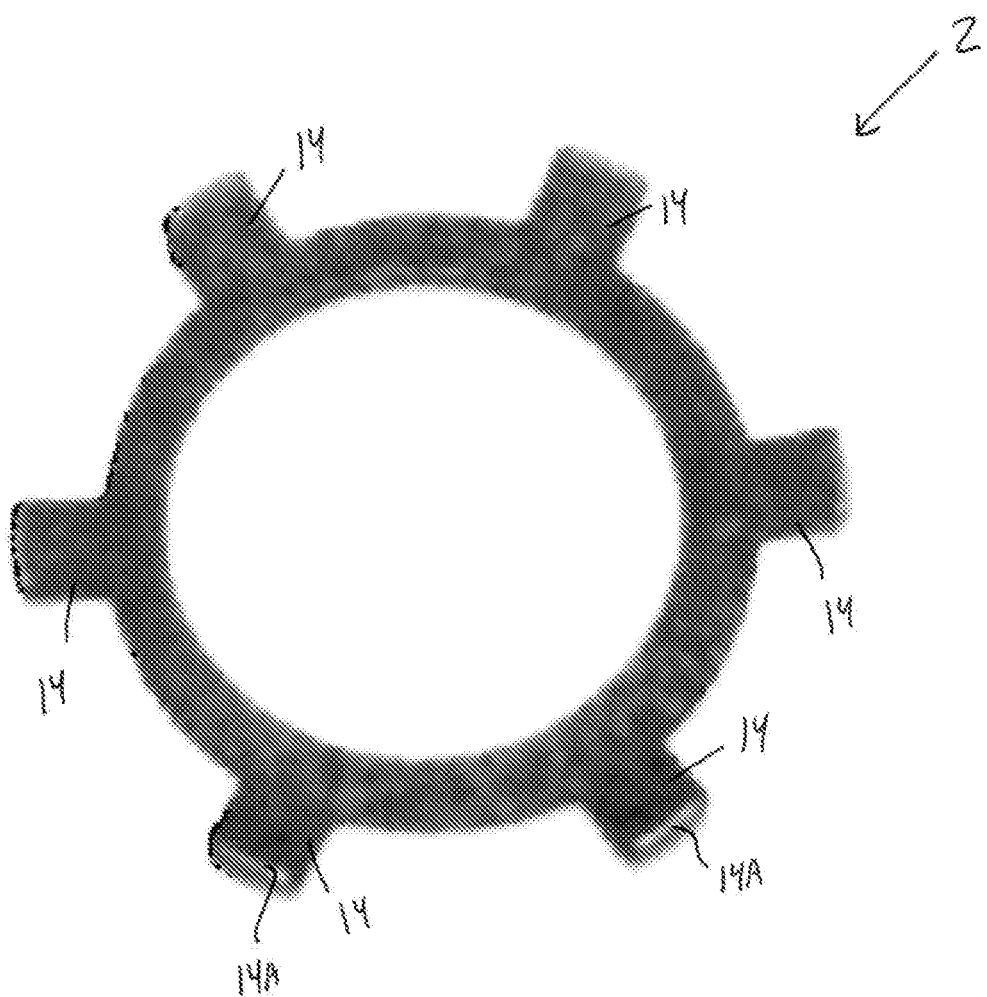
FIG. 5 is a perspective view of yet another compression element in accordance with certain embodiments.

FIG. 5 illustrates yet another embodiment of a compression element 2 with an interrupted interference edge, wherein the compression element 2 includes a plurality of radial protrusions 14 that extend radially outwardly from the main body of the compression element as shown. The radial protrusions 14 are generally flat and act as radial teeth. In the embodiment shown, there are six spaced radial protrusions 14, although those skilled in the art will appreciate that fewer or more could be present. Preferably the radial protrusions 14 are equally spaced from one another. In this embodiment, the radial outer edge 14A of one or more of the radial protrusions 14 is bent upwardly, facing away from the sealing element 3 when properly positioned in a well 10. The bent radial outer edge 14A further inhibits axial movement away from the sealing gasket 3 by digging into the well wall 1 should force be applied in that axial direction.

In some embodiments, the sealing member and compression element may be integrated. For example, FIGS. 6A and 6B illustrate an embodiment where compression element 2' and sealing element 3' are over-molded to form an integrated piece. In certain embodiments the sealing element 3' is a thermoplastic elastomer which bonds or fuses to the compression element. To enhance the bonding or fusion, a groove 30 can be provided in the compression element 2' to increase the surface area available for bonding or fusing. In some embodiments (FIG. 6B), the interference fit with the wall 1 of the well 10 is created with an interrupted interference edge, wherein the compression element 2' includes a plurality of spaced radial protrusions or lobes or teeth 13' that extend radially outwardly from the main body of the compression element. In other embodiments (FIG. 6A), the interference fit is created with an interference edge of constant diameter.

Another integrated embodiment of the sealing member and compression element is shown in FIG. 7. An elastomer over-mold material such as LSR (liquid silicone rubber) may be used as the compression element 2", but this may have minimal adhesion or fusion to the sealing element 3". Accordingly, the sealing element 3" may be encapsulated in the compression element 2", using feed through holes 65 connecting the upper and lower sealing element material so that it is physically trapped by the elastomeric compression element 2". Accordingly, groove is formed on the top and bottom surface of the compression ring. Those two grooves are connect by through holes through the part so that when the compression element 2" is over-molded, the bottom groove fills and forms the sealing face, the holes feed to the top groove which fills and provides a lock so that the compression element 2" is entrapped onto and inside the sealing element 3", effectively creating a buttoning of the two parts (See also FIG. 8B).

FIGS. 8A, 8B and 8C also illustrate an integrated embodiment of the sealing member and compression element. In this embodiment, the sealing element 3''' is also entrapped or encapsulated in the compression element 2''', and the compression element includes one or more openings 26 in the annular side wall to allow liquid that has collected between the well wall and the compression member 2''' to escape and be filtered by the membrane, thus reducing the amount of lost liquid volume during use.

Figure 9B:
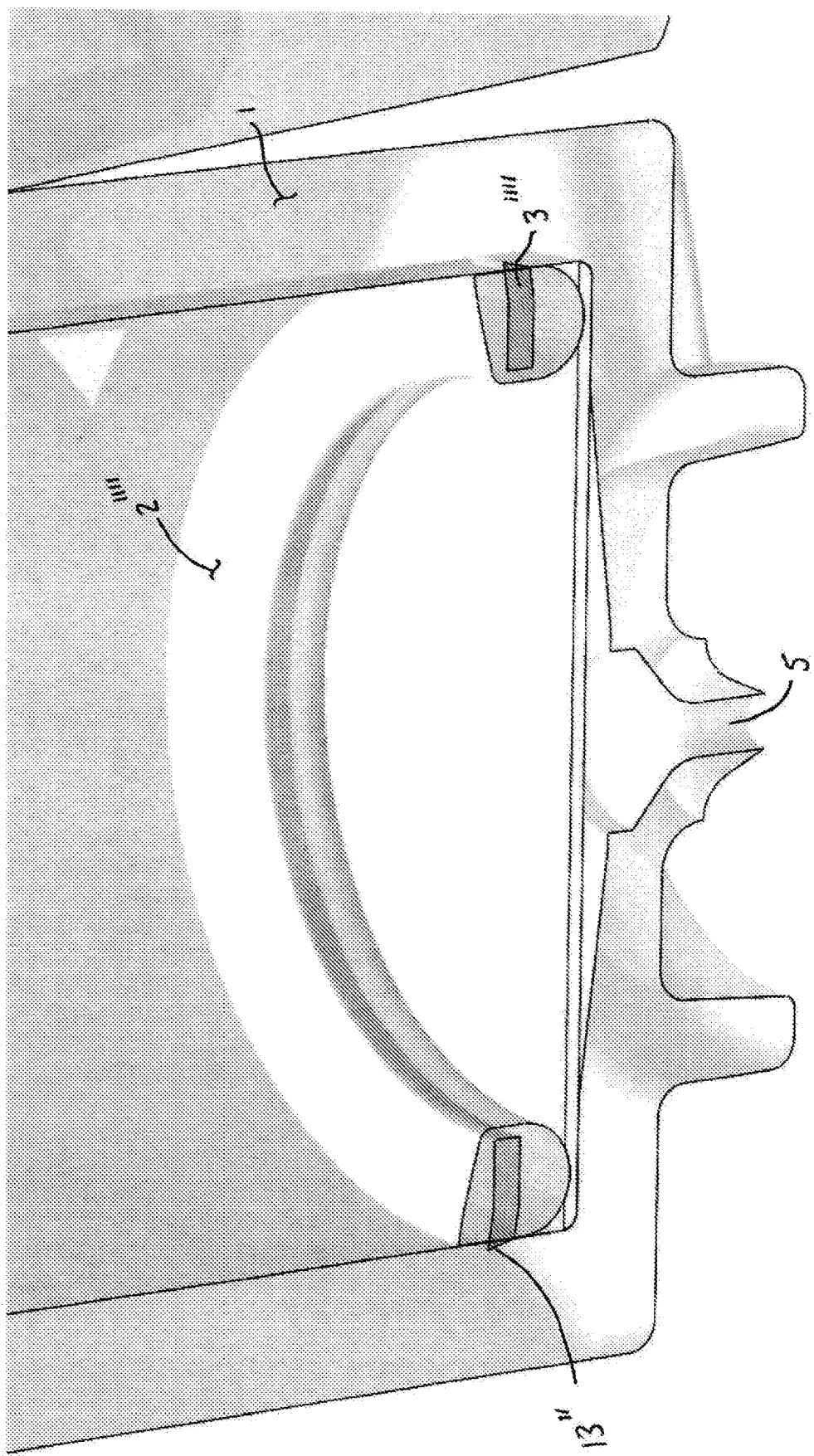
FIG. 9B is a perspective view of the integrated compression element and sealing member of FIG. 9A positioned in a well.

FIGS. 9A 9B and 9C also illustrate an integrated embodiment of the sealing member and compression element. In this embodiment, a metal insert is encapsulated in an elastomer such as liquid inject silicone or a thermoplastic elastomer. The metal provides rigidity for insertion into the well while maintaining a low profile. In the embodiment shown, spaced radial protrusions or lobes or teeth 13" that extend radially outwardly from the main body of the compression element are provided to create the interference fit with the inner wall of the well. Since the radial protrusions 13' are of metal, a sharp edge can be provided to ensure effective engagement with the well wall.

FIG. 10 illustrates yet another alternative embodiment. In the embodiment shown, the well 10 is one of a plurality of wells (e.g., one well of a multiwell filtration element or device 100 having, for example, 12, 24, 96 or 384 wells), although a single well device could be used. The multiwell filtration element may be made of a polymeric material typically used for such devices, such as a polyolefin (e.g., polypropylene, polyethylene), polycarbonate, acrylics, polystyrene, etc. A porous filter material or membrane 4 is sized to be positioned in the well 10, typically in proximity to the outlet so as to cover the second opening 15, and typically supported on filter support such as an annular support member 16 and radial ribs 16' or the like. More than one porous filter material or membrane 4 may be used in each well 10. If a plurality of membranes is used, such as in a layered format, membranes in a layer may have the same or different pore sizes from other membranes in a layer. Depth filters also may be used. In certain embodiments, a pliable seal or sealing member 3, such as a flat gasket or O-ring, is positioned in the at least one well 10 on a portion of the porous filter material 4, such as about the perimeter of the porous filter material 4. The sealing member 3 may be positioned in the well 10 so that it may be in compressive relationship with the top surface or face of the porous filter material 4.

In the embodiment shown, the compression element 2 includes an internal well sleeve or insert 200 positionable in a well 10 to compress the sealing member 3 so that the sealing member 3 contacts both the porous filter material 4 and the well wall 1 internal surface (as well as the contact points of the compression element 200). In certain embodiments, each internal well insert is an elongated sleeve that corresponds to the configuration of the internal volume of the well 10 in which it is to be inserted. For example, where the well 10 has a generally cylindrical internal volume, the internal well insert 200 may be an elongated cylinder with an outer cylindrical wall 201 having an outside diameter slightly less than the inside diameter of the well internal volume region. In certain embodiments, the outside diameter of the internal well insert 200 tapers radially inwardly from the top surface to the bottom surface, preferably tapering uniformly. Accordingly, the outside diameter at the top or upper portion of the internal well insert 200 is larger than the outside diameter at the bottom or lower portion of the internal well insert 200. In some embodiments, the insert may be generally conical.

The internal well insert 200 is independent of the porous filter material 4 thickness or chemistry.

The internal well insert 200 may be affixed in place in a well 10, such as by bonding it to a support surface of the substrate or plate in which the well 10 or wells are formed, such as a top surface of the substrate. As a result, the positional relationship between the internal well insert 200 and the sealing member 3 is maintained. The internal well insert 200 thus functions to hold the sealing member 3 in place in the well 10, apply a force to the sealing member 3 so that it seals on the face of the porous filter material 4, and push the sealing member radially outwardly to seal against the well wall 1 inside surface in a liquid-tight manner so that liquid sample cannot flow around the porous filter material 4 and out the outlet without passing through the porous filter material 4.

In embodiments where the device has multiple wells 10, preferably the number of internal well inserts 200 equals the number of wells 10, so that each well 10 has a respective internal well insert 200.

In certain embodiments, the configuration of each internal well insert 200 generally matches the configuration of a respective well 10 in which it is to be introduced. For example, for wells 10 with circular cross-sections, the region of the internal well insert 200 that occupies the internal volume of the well 10 also may have a circular cross-section. The outside diameter of the region of internal well insert 200 that occupies the internal volume of the well 10 should coincide with the contour of the well wall 1, and should be slightly less than the inside diameter of the corresponding regions of the well 10, so that when the internal well insert 200 is introduced into the well 10 and affixed in its operative position, the outside wall of the internal well insert 200 abuts against the well wall 1. Thus, the internal volume of the internal well insert 200 becomes the flow channel in the well 10 of the filtration device 100, and the inlet of the internal well insert 200 becomes the inlet of the well 10. By varying the height of the internal well insert 200, the effective volume of a well can be varied. Thus, the volume of a well effectively can be increased by increasing the height of the internal well insert 200 so that it extends axially to a further extent out of the well 10, without changing the multiwell format (e.g., retaining the automation compatible 96-well format).

Other shapes typical of single well or multiwell formats are within the scope of the embodiments disclosed herein, including wells with square and honeycomb cross-sections.

Figure 18B:
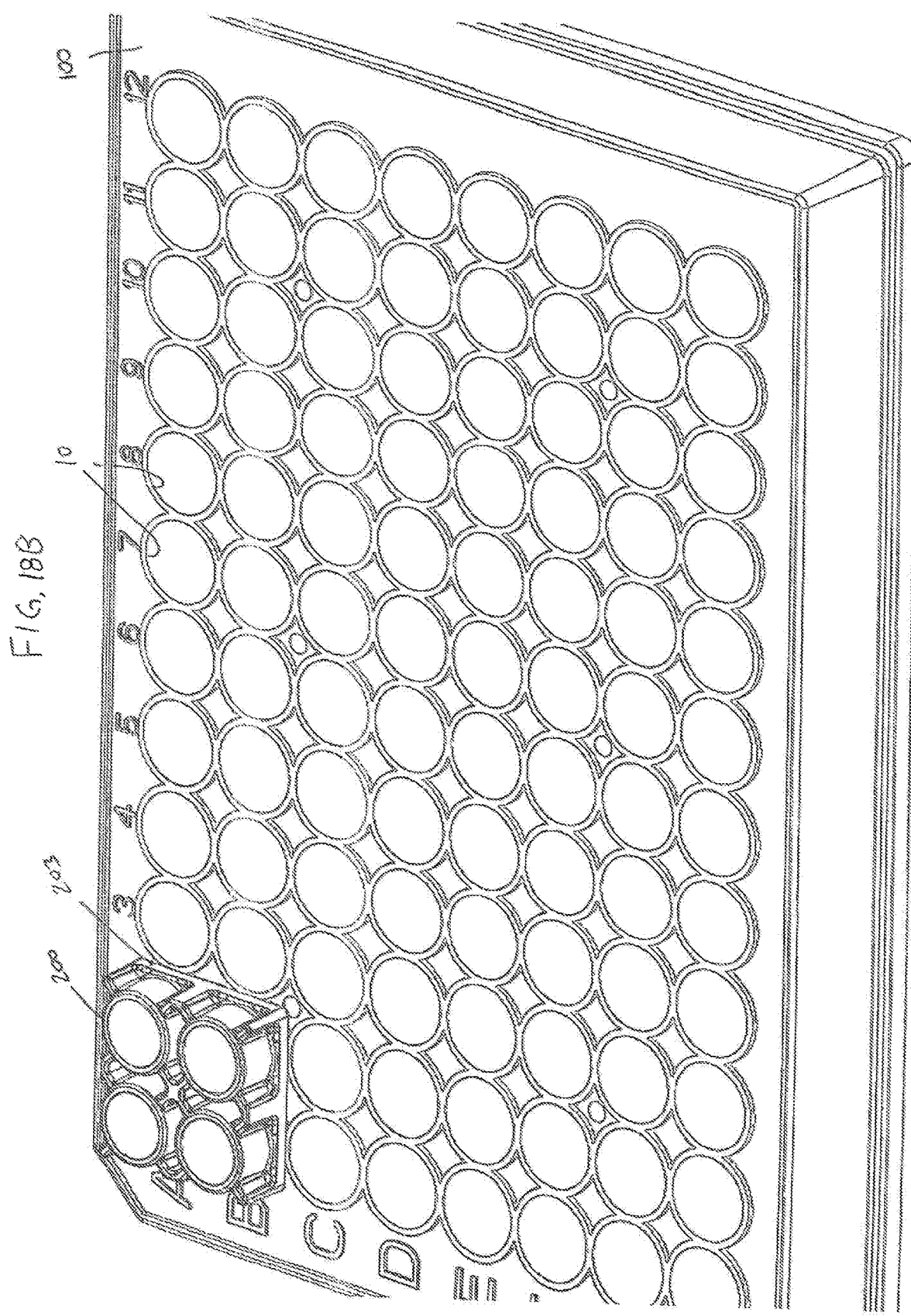
FIG. 18B is a perspective view of a multiwell plate with a 2×2 array of internal well sleeves or inserts shown inserted into respective wells in accordance with certain embodiments.

In certain embodiments, as best seen in FIGS. 18B and 19, each internal well insert 200, when positioned within a respective well 100 in the assembled condition, extends axially above the well 10. That is, the axial length of an internal well insert 200 is greater than the axial depth of a well 10. In certain embodiments, the internal well insert 200 may be of a variable/adjustable length to accommodate different desirable volumes.

In embodiments where the device has multiple wells 10 and multiple internal well inserts 200 are used, each internal well insert 200 may be an individual and independent unit, or more than one internal well inserts 200 may be an integral assembly. For example, four internal well inserts 200 may be formed or attached in an integral 2×2 array (FIGS. 18A and 18B), or an a 1×4 linear array; or sixteen internal well inserts 200 may be formed in an integral 4×4 array (FIG. 19). FIG. 20 shows an embodiment where a single array that is 12×8 is used in a 96-well multiwell filtration device 100. In certain embodiments where arrays of inserts are provided, the arrays may have an outer perimeter wall 203 that sits on the top surface of the multiwell filtration device 100. This perimeter wall 203 may thus a stop face A (FIG. 11) that abuts against top surface B of the filtration device 100 to prevent further insertion of the internal well insert(s) into well(s). The arrays need not be symmetrical; a 1×3, 2×3 or 4×6 arrays, for example, could be used. Similarly, a single integral unit including all of the internal well inserts 200 (e.g., 96 for a 96 well multiwall plate, or 384 for a 384 well multiwall plate) could be used.

In some embodiments, the face or free end of the internal well insert 200 that contacts the sealing member 3 is angled or sloped towards the well wall 1, as seen in FIG. 13. Thus, in the embodiment shown, when the internal well insert 200 is positioned in place in the well 10, the region 200A of the internal well insert 200 that abuts the well wall 1 extends into the well 10 to a slightly lesser extent than the radially innermost region 200B. This slope helps bias the sealing member 3 to seal against the wall 1 and to the face of the membrane or porous filter material 4 when the sealing member 3 is compressed.

In certain embodiments, as best seen in FIG. 11, the internal well insert 200 includes an attachment element 7 or protrusion. As best seen in FIG. 11, the attachment element 7 is an axially extending protrusion. In the embodiment shown, the axially extending protrusion or attachment element 7 is triangular in cross-section, tapering to a pointed free end 7A. The position of FIG. 11 where this tapered free end 7A abuts against an attachment surface 6 of the substrate in which the wells 10 are formed is the start position to initiate the ultrasonic welding process. In some embodiments, the attachment element 7 may be heat bonded, fused or otherwise affixed to the substrate surface as seen at 19 in FIG. 12, to permanently affix the internal well insert 200 in place in the well 10 in its proper operative position, where it provides the necessary force to compress the sealing member 3 between the internal well wall 1 and the membrane or porous filter material 4 sufficient to achieve a seal and prevent any fluid from leaking around the sealing member 3. In certain embodiments, attachment points on the surface of the multiwell filtration device 100 are in regions between wells 10.

In certain embodiments, the internal well insert 200 is constructed of the same or similar material as the substrate in which the wells 10 are formed; the important issue being that the materials be compatible with ultrasonic welding. This allows the internal well insert 200 to be thermally fused to the substrate such as through the use of ultrasonic energy.

Figure 17:
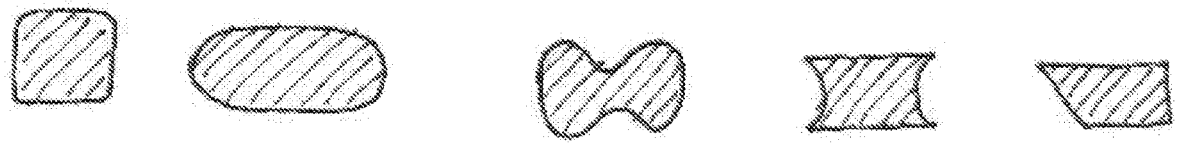
FIG. 17 are cross-sectional views of various seals in accordance with certain embodiments.

The sealing member 3 in any of the embodiments discussed above may be an O-ring having a circular cross-section, a die cut flat sheet gasket material, or a custom molded elastomeric seal, having a cross-section as shown in FIG. 17. These could be cut by several different means, e.g., die cut, waterjet, laser, etc. Alternatively, the sealing member 3 may be an elastomeric seal over-molded onto the internal wall insert 200, or any other gasket suitable for the application.

The embodiment of FIG. 10 may be assembled as follows. A porous filter material 4, such as a membrane, may be die cut into a disc and placed at the bottom of a well 10, covering the well outlet or second opening 15. A seal or sealing member 3 such as a gasket or an O-ring is positioned on top of the membrane (i.e., the upstream filtration side) in the well 10. The internal well insert 200 is inserted into the well 10 to a location in the well 10 where it contacts the sealing element 3, causing the sealing element 3 to compress against the porous filter material 4, the well wall 1 and the surface(s) of the internal well insert 200 contacting the sealing member 3. The internal well insert 200 may then be affixed in place, such as by welding, bonding, adhering or otherwise affixing it to the substrate in which the wells 10 are formed, e.g., the top surface of a multiwell filtration device 100.

The internal well insert 200 may be attached to the substrate in alternative ways, such as that shown in FIG. 14. The embodiment of FIG. 14 is a mechanical attachment, and includes a snap feature 80 having a single fixed catch position with a corresponding receiver geometry 90 on an attachment surface of the filtration device substrate. The snap feature 80 has an axially extending arm 81 with a notch formed at 82. As the internal well insert 200 is introduced axially into a well 10, the snap feature 80 extends into and through an opening 101 in the filtration device, and the pliability or flexibility of the arm 81 allows it to be initially forced radially to the right in FIG. 14 by the free end of receiver 90, as shown by arrow 83. Once the receiver geometry 90 is cleared by the snap feature 80, the arm 81 snaps back (radially to the left in FIG. 14 and in the opposite direction of arrow 83) and locks underneath the receiver 90, affixing the internal well insert 200 in place in its operative position.

Figure 15:
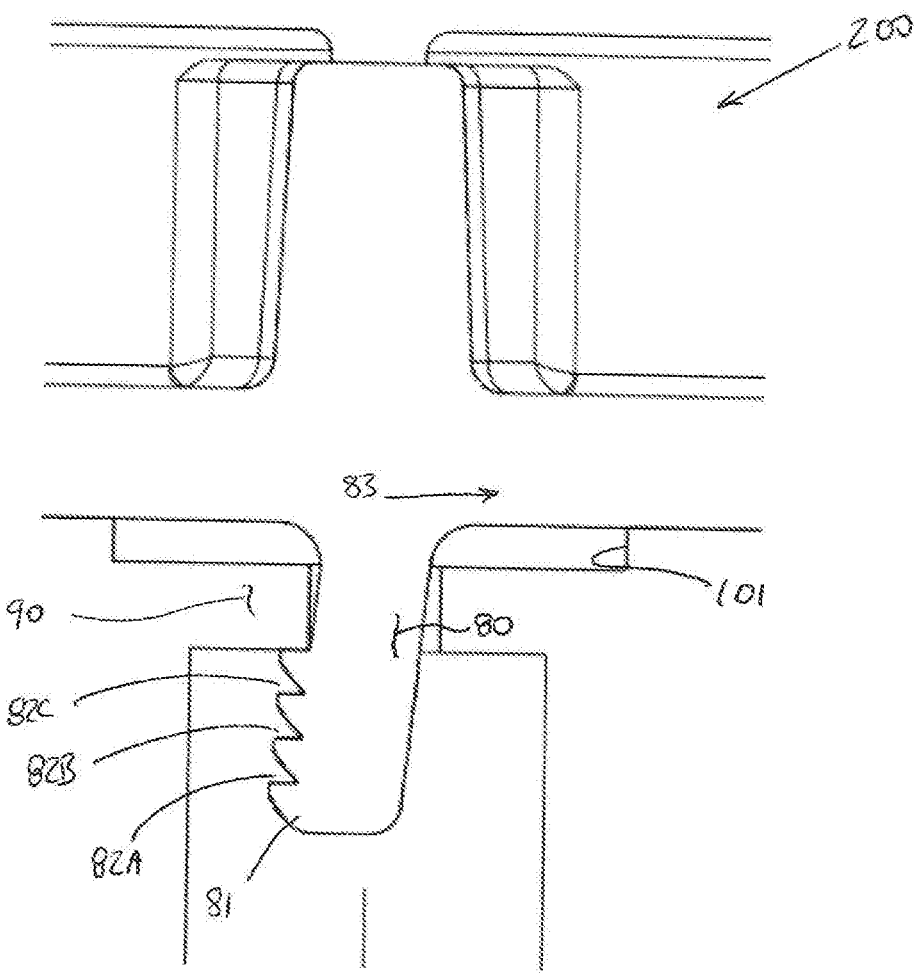
FIG. 15 is a cross-sectional view of an internal well sleeve or insert with an alternative snap feature for attaching it to a well substrate in accordance with certain embodiments.

FIG. 15 illustrates a similar embodiment, except that multiple notches 82A, 82B, 82C are formed in the arm 81. The notches may function similarly to a ratchet. Although three such notches are shown, those skilled in the art will appreciate that the number of notches is not particularly limited; fewer or more than three notches could be used. The presence of multiple notches allows the accommodation of varied membrane 4 thicknesses and compression requirements by allowing the internal well insert 200 to be inserted to different depths in the well 10, depending upon which notch engages with the receiver geometry 90.

Figure 16:
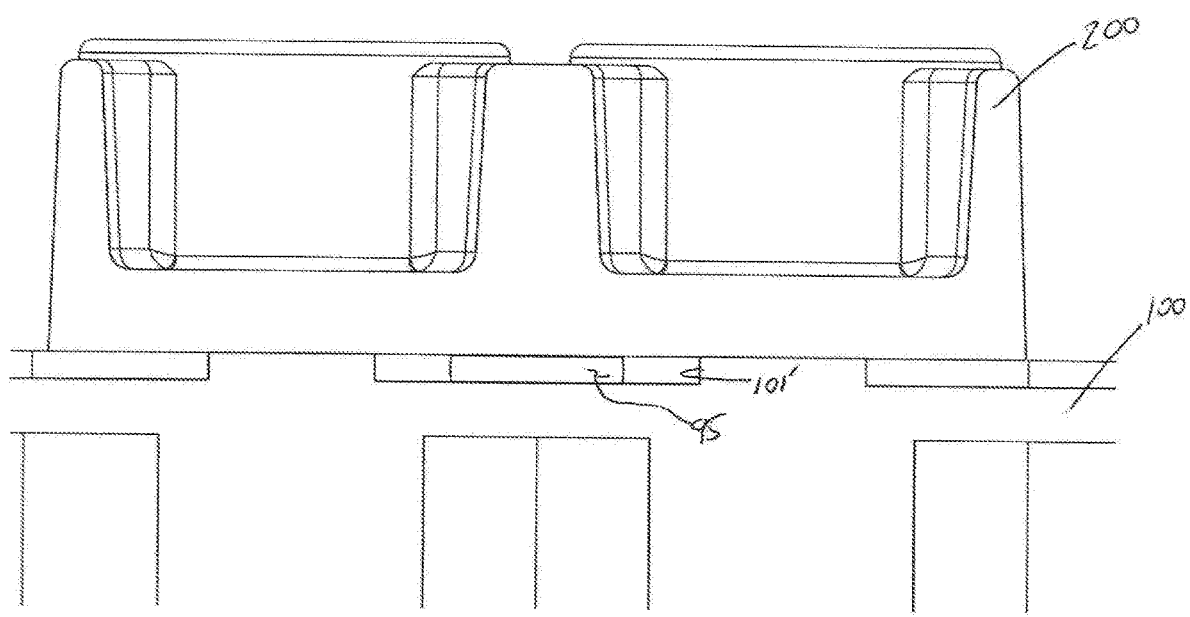
FIG. 16 is a cross-sectional view of an internal wall insert attached to a well substrate with an adhesive in accordance with certain embodiments.

FIG. 16 illustrates attaching the internal well insert 200 to the substrate in which the wells 10 are formed with an adhesive 95. Suitable adhesives include commercially available UV curable adhesives, thermally curable adhesives, and two-part chemical adhesives. Examples include LOCTITE 3936, LOCTITE EA E-60 HP and E-30CL, etc. As can be seen in the embodiment of FIG. 16, a recessed region 101' can be formed in the top surface of the filtration device (e.g., the top surface of a multiwall device 100) to accommodate the adhesive 95 and make it available for attachment to the internal well insert 200.

In all cases, the mechanism or mechanisms used to attach the internal well insert 200 should be provided in sufficient number and locations to produce consistent force across the entire quantity of wells 10 to achieve equal sealing compressive force in all wells 10 of the device. Different attachment mechanisms may be used in the same device to accomplish this objective.

Suitable applications for the filtration apparatus of the embodiments disclosed herein are many, and include basic sample preparation, including those that involve a driving force such as vacuum, pressure or centrifugation. Applications also include free versus bound drug assays. These assays investigate the availability of the drug once introduced into a patient. They specifically look at the amount of the drug that is not bound and is available to act on the desired site. For example, the drug of interest is spiked into a blood product such a serum, incubated, and then centrifuged through an ultrafiltration membrane. The ultrafiltration membrane retains the blood or serum products and any non-bound drug freely passes through the membrane and is collected. The collected filtrate is tested and a ratio of bound versus free is determined.

While the embodiments described herein include a limited number of embodiments, these specific embodiments are not intended to limit the scope as otherwise described and claimed herein. Modification and variations from the described embodiments exist. The following example is given as a specific illustration of embodiments disclosed, and it should be understood that the embodiments disclosed are not limited to the specific details set forth in the example.

Example 1

Figure 21:
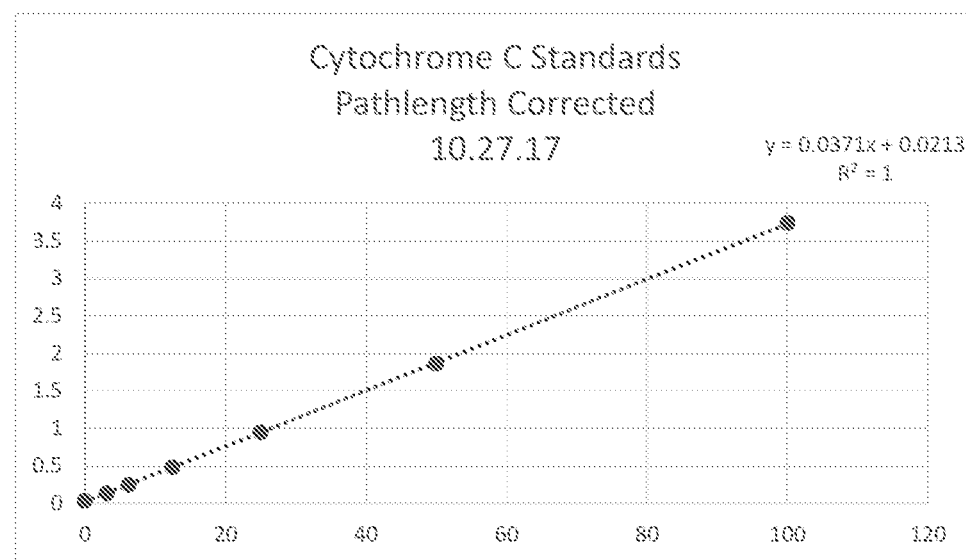
FIG. 21 is a graph of percent Cytochrome-C in filtrate in accordance with Example 1.

A 96 well plate made of polypropylene was assembled as per embodiments disclosed herein, using ULTRACEL membranes commercially available from MilliporeSigma, with a molecular weight cut-off of 10K and about 0.010 inches thick. O-rings were used as the sealing member. Twenty-four 2×2 arrays of internal well inserts were welded into position so as to compress the O-rings in each respective well and seal the membrane face within each well.
Test Method Set Up:
96 WELL PLATE
Absorbance Endpoint
Full Plate
Wavelengths: 410
Pathlength Correction: 977/900
  Absorbance at 1 cm: 0.18
Read Speed: Normal, Delay: 100 msec, Measurements/Data Point: 8
Percent Cytochrome-C in filtrate calculated from standard curve.
The first plate results show that the seal can work. This plate was handmade with minimal control on the weld depth. The graph in FIG. 21 shows the standard curve for the Cytochrome-C. The following (2) tables are the % of protein retained. We see that all but one well in each plate was fully retentive, meaning greater than 90% of the protein was retained which is confirmation of seal integrity.

|   | 1 | 2 | 3 | 4 | 5 | 6 | 7 | 8 | 9 | 10 | 11 | 12 |
|---|---|---|---|---|---|---|---|---|---|---|---|---|
| Plate 1 | | | | | | | | | | | | |
| A | 97 | 98 | 97 | 97 | 98 | 98 | 98 | 97 | 98 | 98 | 98 | 94 |
| B | 97 | 98 | 98 | 98 | 98 | 98 | 97 | 97 | 98 | 98 | 98 | 98 |
| C | 97 | 97 | 97 | 98 | 98 | 98 | 97 | 97 | 97 | 98 | 96 | 97 |
| D | 95 | 97 | 98 | 98 | 98 | 97 | 97 | 97 | 97 | 97 | 97 | 98 |
| E | 95 | 97 | 98 | 96 | 96 | 96 | 96 | 96 | 97 | 97 | 97 | 97 |
| F | 97 | 97 | 97 | 97 | 97 | 96 | 97 | 95 | 96 | 97 | 97 | 96 |
| G | 97 | 97 | 97 | 97 | 98 | 97 | 97 | 98 | 97 | 96 | 97 | 96 |
| H | 97 | 97 | 98 | 97 | 97 | 98 | 97 | 97 | 98 | 98 | 98 | |
| Plate 2 | | | | | | | | | | | | |
| A | 98 | 98 | 98 | 98 | 98 | 98 | 98 | 98 | 97 | 95 | 97 | 97 |
| B | | 98 | 98 | 98 | 97 | 98 | 97 | 97 | 97 | 96 | 96 | 96 |
| C | 97 | 97 | 98 | 97 | 96 | 96 | 97 | 96 | 96 | 96 | 95 | 94 |
| D | 97 | 96 | 97 | 97 | 97 | 96 | 97 | 97 | 96 | 95 | 95 | 95 |
| E | 97 | 97 | 97 | 97 | 96 | 97 | 75 | 97 | 97 | 95 | 94 | 95 |
| F | 97 | 97 | 97 | 97 | 97 | 97 | 97 | 95 | 97 | 96 | 96 | 93 |
| G | 98 | 98 | 97 | 98 | 98 | 97 | 98 | 97 | 98 | 98 | 97 | 96 |
| H | 97 | 97 | 98 | 98 | 98 | 98 | 97 | 96 | 98 | 98 | 98 | 97 |

What is claimed is:

1. A filtration apparatus comprising:
a substrate having a well defined by a well wall, said well having an interior surface and a first opening and a second opening spaced from said first opening and defining a well volume there between;
a porous filter material in said well, positioned in said well so as to cover said second opening;
a seal in said well positioned on a portion of said porous filter; and
a compression element fixed in said well in a position to compress said seal into sealing relationship with said porous filter and against said interior surface of said wall of said well; said compression element being dimensioned to create an interference fit with said wall of said well to fix said compression element in said well.

2. The filtration apparatus of claim 1, wherein said substrate comprises a plurality of wells each defined by a well wall having an interior surface; a respective porous filter element in each of said plurality of wells; and a respective seal in each of said plurality of wells positioned on a portion of said respective porous filter; said apparatus further comprising a respective compression element fixed in each of said plurality of wells in a position to compress said respective seal in each of said plurality of wells into sealing relationship with said respective porous filter and against said interior surface of each wall of each of said plurality of wells; each said respective compression element being dimensioned to create an interference fit with each said wall of each said well to respectively fix each said respective compression element in each of said plurality of wells.

3. The filtration apparatus of claim 1, wherein said compression element of said well and said seal of said well are one piece.

4. The filtration apparatus of claim 1, wherein said seal is an O-ring.

5. The filtration apparatus of claim 1, wherein said compression element of said well has a plurality of radial protrusions which create said interference fit.

6. The filtration apparatus of claim 1 wherein said compression element of said well encapsulates at least a portion of said seal.

7. The filtration apparatus of claim 6, wherein said seal of said well encapsulates at least a portion of the compressive element.

8. The filtration apparatus of claim 1, wherein said seal of said well encapsulates at least a portion of the compressive element.

9. The filtration apparatus of claim 1, wherein said porous filter material of said well comprises a membrane.

10. The filtration apparatus of claim 1, wherein said porous filter material of said well comprises a plurality of membranes.

11. The filtration apparatus of claim 10, wherein each one of said plurality of membranes has a different pore size than another of said plurality of membranes.

12. A filtration apparatus comprising:
a substrate having a well defined by a well wall, said well having an interior surface and a first opening and a second opening spaced from said first opening and defining a well volume there between;
a porous filter material in said well, positioned in said well so as to cover said second opening;
a seal in said well positioned on a portion of said porous filter; and
an internal well insert coupled to said substrate, said internal well insert at least partially disposed in said well and positioned in said well so as to compress said seal into sealing relationship with said porous filter and said well wall, said internal well insert having an angled free end having a region that contacts said seal and abuts said well wall, whereby said region that contacts said seal and abuts said well wall extends into said well to a lesser extent than a radially innermost region of said angled free end of said internal well insert.

13. The filtration apparatus of claim 12, wherein said internal well insert has a tapered free end that compresses said seal.

14. The filtration apparatus of claim 12, wherein said seal of said well is an O-ring.

15. The filtration apparatus of claim 12, wherein said porous filter material of said well comprises a membrane.

16. The filtration apparatus of claim 12, wherein said porous filter material of said well comprises a plurality of membranes.

17. The filtration apparatus of claim 16, wherein each one of said plurality of membranes has a different pore size than another of said plurality of membranes.

18. The filtration apparatus of claim 12, wherein said internal well insert is coupled to said substrate by heat bonding, ultrasonic welding, with an adhesive, or by mechanical attachment.

19. The filtration apparatus of claim 12, wherein said internal well insert has a height sufficient to extend axially above said first opening of said well.

20. A filtration apparatus comprising:
a substrate having a plurality of wells, each well defined by a well wall and having a first opening and a second opening spaced from said first opening and defining a well volume there between;
at least one porous filter disposed in each well, positioned in each well so as to cover said second opening;
a seal in each said well positioned on a portion of said porous filter; and
a plurality of internal well inserts coupled to said substrate, the number of said internal well inserts corresponding to the number of said plurality of wells, each internal well insert being at least partially disposed in a respective well and positioned in said respective well so as to compress said seal into sealing relationship with said porous filter and said well wall, each said internal well insert having an angled free end having a region that contacts said seal and abuts said well wall, whereby said region that contacts said seal and abuts said well extends into said well to a lesser extent than a radially innermost region of said free end of said internal well insert.

21. The filtration apparatus of claim 20, wherein at least some of said plurality of internal well inserts are coupled to one another in an array.

22. The filtration apparatus of claim 20, wherein each of said plurality of internal well inserts is coupled to said substrate by heat bonding.

23. The filtration apparatus of claim 20, wherein each of said plurality of internal well inserts is coupled to said substrate by ultrasonic welding.

24. The filtration apparatus of claim 20, wherein each of said plurality of internal well inserts is coupled to said substrate with an adhesive.

25. The filtration apparatus of claim 20, wherein each of said plurality of internal well inserts is coupled to said substrate by mechanical attachment.

26. The filtration apparatus of claim 20, wherein there are a plurality of porous filters disposed in each well, and wherein at least one of said plurality of porous filters has a pore size different from at least one other of said plurality of porous filters.

27. The filtration apparatus of claim 20, wherein each said internal well insert has a height sufficient to extend axially above said first opening of said well.

28. The filtration apparatus of claim 20, wherein each said internal well insert has a top surface, a bottom surface and an outside diameter, the outside diameter tapering radially inwardly from the top surface to the bottom surface.

29. The filtration apparatus of claim 28, wherein said outside diameter tapers uniformly.

30. A method of filtering a sample with a filtration device comprising a substrate having a well defined by a well wall, said well having an interior surface and a first opening and a second opening spaced from said first opening and defining a volume there between, a porous filter material in said well, positioned in said well so as to cover said second opening, a seal in said well positioned on a portion of said porous filter, and an internal well insert coupled to said substrate and disposed within said well; said internal well insert having a wall that abuts against said well wall and an angled free end having a region that contacts said seal, whereby said region extends into said well to a lesser extent than a radially innermost region of said free end of said internal well insert, said method comprising:
introducing said sample into said internal well insert, and filtering said sample through said porous filter material.

31. The method of claim 30, further comprising applying a driving force to said device to filter said sample through said porous filter material.

32. A method of forming a filtration device, comprising:
providing a substrate having a well defined by a well wall, said well having a first opening and a second opening spaced from said first opening and defining a volume there between;
positioning a porous filter material in said well so as to cover said second opening;
positioning a seal in said well on a portion of said porous filter;
introducing an internal well insert into said well, said internal well insert having an angled free end having a region that contacts said seal and abuts said well wall, whereby said region extends into said well to a lesser extent than a radially innermost region of said free end of said internal well insert so as to compress said seal against said porous filter material.

* * * * *